(12) United States Patent
Thornton

(10) Patent No.: US 8,316,858 B2
(45) Date of Patent: Nov. 27, 2012

(54) SYSTEM FOR COUPLING AN ORAL APPLIANCE TO A MEDICAL MASK

(75) Inventor: W. Keith Thornton, Dallas, TX (US)

(73) Assignee: AirWay Technologies, LLC, Carrollton, TX (US)

( * ) Notice: Subject to any disclaimer, the term of this patent is extended or adjusted under 35 U.S.C. 154(b) by 0 days.

(21) Appl. No.: 12/795,373

(22) Filed: Jun. 7, 2010

(65) Prior Publication Data

US 2010/0263677 A1 Oct. 21, 2010

Related U.S. Application Data

(63) Continuation-in-part of application No. 11/278,918, filed on Apr. 6, 2006, now Pat. No. 7,748,386.

(51) Int. Cl.
*A61F 5/37* (2006.01)
*A61F 11/08* (2006.01)
*A61C 5/14* (2006.01)
*A61C 3/00* (2006.01)
*A61C 9/00* (2006.01)
*A61C 19/04* (2006.01)
*A61C 17/00* (2006.01)
*A61C 5/00* (2006.01)

(52) U.S. Cl. ........ 128/848; 128/846; 128/859; 128/861; 433/6; 433/37; 433/68; 433/69; 433/80; 433/140; 433/141; 602/902

(58) Field of Classification Search .................. 128/846, 128/848, 859–861, 200.24, 200.27, 200.28; 602/902; 433/6, 37, 68–69, 80, 140, 141
See application file for complete search history.

(56) References Cited

U.S. PATENT DOCUMENTS

| | | | |
|---|---|---|---|
| 339,334 A | 4/1886 | Searle |
| 690,663 A | 1/1902 | Pratt |
| 746,869 A | 12/1903 | Moulton |
| 774,446 A | 11/1904 | Moulton |
| 781,516 A | 1/1905 | Guthrie, Jr. |
| 885,196 A | 4/1908 | Steil |

(Continued)

FOREIGN PATENT DOCUMENTS

DE 156627 12/1904

(Continued)

OTHER PUBLICATIONS

Mayo Clinic Health Letter; Reliable Information for a Healthier Life; *Snoring: Laser Surgery Joins Battle to Restore Peace and Quiet*; vol. 13, No. 7, 8 pages, Jul. 1995.

(Continued)

*Primary Examiner* — Patricia Bianco
*Assistant Examiner* — Brandon L Jackson
(74) *Attorney, Agent, or Firm* — Baker Botts L.L.P.

(57) ABSTRACT

In certain embodiments, an apparatus for treating a breathing condition includes an oral appliance, a mask, and a tensioning device. The oral appliance is configured to receive at least some of a wearer's teeth and a mask. The mask is configured to deliver gas to the wearer. The mask includes a chamber configured to cover the wearer's mouth. The chamber is at least partially enclosed by an interior of the mask. The tensioning device couples the mask to the oral appliance and includes a flexible tension element at least partially disposed between the oral appliance and the mask and within the chamber. The flexible tension element is configured to apply a tensile force between the mask and the oral appliance.

8 Claims, 21 Drawing Sheets

U.S. PATENT DOCUMENTS

| | | | |
|---|---|---|---|
| 893,213 A | 7/1908 | Whiteway |
| 955,562 A | 4/1910 | Thomas |
| 996,783 A | 7/1911 | Moreau |
| 1,076,534 A | 10/1913 | Wallen |
| 1,146,264 A | 7/1915 | Kelly |
| 1,483,694 A | 2/1924 | Stukey |
| 1,592,345 A | 7/1926 | Drager |
| 1,649,664 A | 11/1927 | Carter |
| 1,674,336 A | 6/1928 | King |
| 1,675,202 A | 6/1928 | Warne |
| 1,679,748 A | 8/1928 | Stratton |
| 2,171,695 A | 9/1939 | Harper |
| 2,178,128 A | 10/1939 | Waite |
| 2,383,649 A | 8/1945 | Heidbrink |
| 2,424,533 A | 7/1947 | Faires |
| 2,505,028 A | 4/1950 | Boeger |
| 2,521,039 A | 9/1950 | Carpenter |
| 2,521,084 A | 9/1950 | Oberto |
| 2,531,222 A | 11/1950 | Kesling |
| 2,574,623 A | 11/1951 | Clyde |
| 2,590,118 A | 3/1952 | Oddo, Jr. |
| 2,627,268 A | 2/1953 | Leppich |
| 2,671,446 A | 3/1954 | Mann |
| 2,712,160 A | 7/1955 | Sterczek |
| 2,833,278 A | 5/1958 | Ross |
| 2,867,212 A | 1/1959 | Nunn, Jr. |
| 2,882,893 A | 4/1959 | Godfroy |
| 2,917,045 A | 12/1959 | Schildknecht et al. |
| 2,977,636 A | 4/1961 | McGuire |
| 3,037,501 A | 6/1962 | Miller |
| 3,064,354 A | 11/1962 | Pos |
| 3,107,668 A | 10/1963 | Thompson |
| 3,124,129 A | 3/1964 | Grossberg |
| 3,132,647 A | 5/1964 | Corniello |
| 3,219,033 A | 11/1965 | Wallshein |
| 3,277,892 A | 10/1966 | Tepper |
| 3,312,216 A | 4/1967 | Wallshein |
| 3,321,832 A | 5/1967 | Weisberg |
| 3,330,274 A | 7/1967 | Bennett |
| 3,360,860 A | 1/1968 | Roland |
| 3,434,470 A | 3/1969 | Strickland |
| 3,457,916 A | 7/1969 | Wolicki |
| 3,513,838 A | 5/1970 | Foderick et al. |
| 3,522,805 A | 8/1970 | Wallshein |
| 3,658,058 A | 4/1972 | Neidhart et al. |
| 3,690,004 A | 9/1972 | Frush |
| 3,695,265 A | 10/1972 | Brevik |
| 3,845,768 A | 11/1974 | Garrahan |
| 3,854,208 A | 12/1974 | Arant |
| 3,864,832 A | 2/1975 | Carlson |
| 3,871,370 A | 3/1975 | McDonald |
| 3,882,601 A | 5/1975 | Jahn |
| 3,884,226 A | 5/1975 | Tepper |
| 4,016,650 A | 4/1977 | Leusner et al. |
| 4,026,024 A | 5/1977 | Tradowsky |
| 4,050,457 A | 9/1977 | Davidson |
| 4,114,614 A | 9/1978 | Kesling |
| 4,169,473 A | 10/1979 | Samelson |
| 4,182,312 A | 1/1980 | Mushabac |
| 4,227,877 A | 10/1980 | Tureaud et al. |
| 4,233,972 A | 11/1980 | Hauff et al. |
| 4,258,710 A | 3/1981 | Reber |
| 4,289,127 A | 9/1981 | Nelson |
| 4,294,243 A | 10/1981 | Ernsting et al. |
| 4,304,227 A | 12/1981 | Samelson |
| 4,345,592 A | 8/1982 | Giorgini et al. |
| 4,345,593 A | 8/1982 | Sullivan |
| 4,376,628 A | 3/1983 | Aardse |
| 4,382,783 A | 5/1983 | Rosenberg |
| 4,392,490 A | 7/1983 | Mattingly et al. |
| 4,397,701 A | 8/1983 | Johnson et al. |
| 4,419,992 A | 12/1983 | Chorbajian |
| 4,433,956 A | 2/1984 | Witzig |
| 4,439,147 A | 3/1984 | Magill et al. |
| 4,439,149 A | 3/1984 | Devincenzo |
| 4,454,090 A | 6/1984 | Saumell |
| 4,470,413 A | 9/1984 | Warncke ............... 128/201.18 |
| 4,495,945 A | 1/1985 | Liegner |
| 4,505,672 A | 3/1985 | Kurz |
| 4,530,662 A | 7/1985 | Andersson et al. |
| 4,553,549 A | 11/1985 | Pope et al. |
| 4,568,280 A | 2/1986 | Ahlin |
| 4,569,342 A | 2/1986 | von Nostitz |
| 4,593,686 A | 6/1986 | Lloyd et al. |
| 4,602,905 A | 7/1986 | O'Keefe, III |
| 4,639,220 A | 1/1987 | Nara et al. |
| 4,655,213 A | 4/1987 | Rapoport et al. |
| 4,668,188 A | 5/1987 | Wolfenson et al. |
| 4,669,459 A | 6/1987 | Spiewak et al. |
| 4,676,240 A | 6/1987 | Gardy |
| 4,706,683 A | 11/1987 | Chilton et al. |
| 4,715,368 A | 12/1987 | George |
| 4,741,696 A | 5/1988 | Cetlin |
| 4,773,853 A | 9/1988 | Kussick |
| 4,784,123 A | 11/1988 | Robeson |
| 4,799,500 A | 1/1989 | Newbury |
| 4,858,605 A | 8/1989 | Levy |
| 4,858,606 A | 8/1989 | Hamlin |
| 4,862,903 A | 9/1989 | Campbell |
| 4,870,962 A | 10/1989 | Sitnik |
| 4,886,056 A | 12/1989 | Simpson |
| 4,892,478 A | 1/1990 | Tateosian et al. |
| 4,901,737 A | 2/1990 | Toone |
| 4,906,234 A | 3/1990 | Voychehovski |
| 4,919,128 A | 4/1990 | Kopala et al. |
| 4,932,867 A | 6/1990 | Ueno |
| 4,941,212 A | 7/1990 | Liff |
| 4,955,393 A | 9/1990 | Adell |
| RE33,442 E | 11/1990 | George |
| 5,003,994 A | 4/1991 | Cook |
| 5,011,407 A | 4/1991 | Pelerin |
| 5,018,533 A | 5/1991 | Hawkins |
| 5,026,278 A | 6/1991 | Oxman et al. |
| 5,028,232 A | 7/1991 | Snow |
| 5,040,976 A | 8/1991 | Ubel, III et al. |
| 5,042,478 A | 8/1991 | Kopala et al. |
| 5,042,506 A | 8/1991 | Liberati |
| 5,046,512 A | 9/1991 | Murchie |
| 5,052,409 A | 10/1991 | Tepper |
| 5,055,039 A | 10/1991 | Abbatte et al. |
| 5,056,534 A | 10/1991 | Wright |
| 5,062,421 A | 11/1991 | Burns et al. |
| 5,064,371 A | 11/1991 | Smeltzer |
| 5,065,756 A | 11/1991 | Rapoport |
| 5,066,231 A | 11/1991 | Oxman et al. |
| 5,078,600 A | 1/1992 | Austin |
| 5,092,346 A | 3/1992 | Hays et al. |
| 5,103,838 A | 4/1992 | Yousif |
| 5,112,225 A | 5/1992 | Diesso |
| 5,117,816 A | 6/1992 | Shapiro et al. |
| 5,154,184 A | 10/1992 | Alvarez |
| 5,154,609 A | 10/1992 | George |
| 5,183,057 A | 2/1993 | Syrop et al. |
| 5,188,529 A | 2/1993 | Lüth |
| 5,190,457 A | 3/1993 | Schreinemakers |
| 5,193,532 A | 3/1993 | Moa et al. |
| 5,213,498 A | 5/1993 | Pelerin |
| 5,233,978 A | 8/1993 | Callaway |
| 5,243,971 A | 9/1993 | Sullivan et al. |
| 5,243,972 A | 9/1993 | Huang |
| 5,245,995 A | 9/1993 | Sullivan et al. |
| 5,265,595 A | 11/1993 | Rudolph |
| 5,267,557 A | 12/1993 | Her-Mou |
| 5,267,862 A | 12/1993 | Parker |
| 5,277,202 A | 1/1994 | Hays |
| 5,284,161 A | 2/1994 | Karell |
| 5,313,960 A | 5/1994 | Tomasi |
| 5,316,020 A | 5/1994 | Truffer |
| 5,320,533 A | 6/1994 | Lee |
| 5,336,086 A | 8/1994 | Simmen et al. |
| 5,365,945 A | 11/1994 | Halstrom |
| 5,370,533 A | 12/1994 | Bushnell |
| 5,373,859 A | 12/1994 | Forney |
| 5,392,773 A | 2/1995 | Bertrand |
| 5,409,017 A | 4/1995 | Lowe |
| 5,415,544 A | 5/1995 | Oxman et al. |
| 5,427,117 A | 6/1995 | Thornton |

| | | |
|---|---|---|
| 5,456,264 A | 10/1995 | Series et al. |
| 5,458,137 A | 10/1995 | Axe et al. |
| 5,474,060 A | 12/1995 | Evans |
| 5,477,850 A | 12/1995 | Zegler et al. |
| 5,499,633 A | 3/1996 | Fenton |
| 5,503,146 A | 4/1996 | Froehlich et al. |
| 5,503,552 A | 4/1996 | Diesso |
| 5,517,983 A | 5/1996 | Deighan et al. |
| 5,537,994 A | 7/1996 | Thornton |
| 5,537,999 A | 7/1996 | Dearman et al. |
| 5,538,000 A | 7/1996 | Rudolph |
| 5,538,014 A | 7/1996 | Wilson et al. |
| 5,540,223 A | 7/1996 | Starr et al. |
| 5,551,419 A | 9/1996 | Froehlich et al. |
| 5,551,872 A | 9/1996 | Mena |
| 5,558,090 A | 9/1996 | James |
| RE35,339 E | 10/1996 | Rapoport |
| 5,560,354 A | 10/1996 | Berthon-Jones et al. |
| 5,562,449 A | 10/1996 | Jacobs et al. |
| 5,566,683 A | 10/1996 | Thornton |
| 5,570,704 A | 11/1996 | Buzzard et al. |
| 5,582,517 A | 12/1996 | Adell |
| 5,592,935 A | 1/1997 | Elstran et al. |
| 5,611,485 A | 3/1997 | Davis |
| 5,657,751 A | 8/1997 | Karr, Jr. |
| 5,657,752 A | 8/1997 | Landis et al. |
| 5,662,101 A | 9/1997 | Ogden et al. |
| 5,676,133 A | 10/1997 | Hickle et al. |
| 5,678,567 A | 10/1997 | Thornton et al. |
| 5,681,164 A | 10/1997 | Bass |
| 5,687,715 A | 11/1997 | Landis et al. |
| 5,713,349 A | 2/1998 | Keaney |
| 5,718,244 A | 2/1998 | Thornton |
| 5,718,500 A | 2/1998 | Vinci guerra et al. |
| 5,720,280 A | 2/1998 | Elstran et al. |
| 5,720,302 A | 2/1998 | Belfer |
| 5,724,965 A | 3/1998 | Handke et al. |
| 5,746,201 A | 5/1998 | Kidd |
| 5,752,510 A | 5/1998 | Goldstein |
| 5,755,219 A | 5/1998 | Thornton |
| 5,807,100 A | 9/1998 | Thornton |
| 5,810,749 A | 9/1998 | Maas |
| 5,829,441 A | 11/1998 | Kidd et al. |
| 5,832,918 A | 11/1998 | Pantino |
| 5,846,082 A | 12/1998 | Thornton |
| 5,887,587 A | 3/1999 | Groenke |
| 5,891,372 A | 4/1999 | Besset et al. |
| 5,954,048 A | 9/1999 | Thornton |
| 5,983,892 A | 11/1999 | Thornton |
| 5,988,166 A | 11/1999 | Hayek |
| 6,012,455 A | 1/2000 | Goldstein |
| 6,083,442 A | 7/2000 | Gabilly |
| 6,109,265 A | 8/2000 | Frantz et al. |
| 6,119,694 A | 9/2000 | Correa et al. |
| 6,123,071 A | 9/2000 | Berthon-Jones et al. |
| 6,155,262 A | 12/2000 | Thornton et al. |
| 6,209,542 B1 | 4/2001 | Thornton |
| 6,247,926 B1 | 6/2001 | Thornton |
| 6,263,871 B1 | 7/2001 | Brown et al. |
| D448,473 S | 9/2001 | Barnett et al. |
| 6,305,376 B1 | 10/2001 | Thornton |
| 6,318,997 B1 | 11/2001 | Mayweather |
| 6,325,064 B1 | 12/2001 | Thornton |
| 6,374,824 B1 | 4/2002 | Thornton |
| 6,405,729 B1 | 6/2002 | Thornton |
| 6,412,488 B1 | 7/2002 | Barnett et al. |
| 6,450,167 B1 | 9/2002 | David et al. |
| 6,464,924 B1 | 10/2002 | Thornton |
| 6,494,206 B1 | 12/2002 | Bergamaschi et al. |
| 6,516,805 B1 | 2/2003 | Thornton |
| 6,571,798 B1 | 6/2003 | Thornton ............... 128/206.21 |
| 6,645,413 B2 | 11/2003 | Jacobs |
| 6,675,802 B1 | 1/2004 | Thornton |
| 6,758,212 B2 | 7/2004 | Swann |
| 6,845,774 B2 | 1/2005 | Gaskell |
| 6,857,428 B2 | 2/2005 | Thornton |
| 6,877,513 B2 | 4/2005 | Scarberry et al. |
| 7,077,138 B2 | 7/2006 | Bateman et al. |
| 7,174,895 B2 | 2/2007 | Thornton et al. |
| 7,597,103 B2 | 10/2009 | Thornton et al. |
| 7,650,885 B2 | 1/2010 | Paoluccio et al. |
| 7,677,889 B2 | 3/2010 | Thornton |
| 7,721,741 B2 | 5/2010 | Thornton |
| 7,748,386 B2 | 7/2010 | Thornton |
| 7,823,590 B2 | 11/2010 | Bibi et al. |
| 7,909,035 B2 | 3/2011 | Thornton |
| 7,963,284 B2 | 6/2011 | Thornton |
| 7,992,558 B2 | 8/2011 | Thornton |
| 8,020,276 B2 | 9/2011 | Thornton |
| 2002/0000230 A1 | 1/2002 | Gaskell |
| 2002/0129818 A1 | 9/2002 | Morgan et al. |
| 2002/0139366 A1 | 10/2002 | Gaschke |
| 2003/0217753 A1 | 11/2003 | Thornton |
| 2003/0234022 A1 | 12/2003 | Belfer |
| 2004/0079374 A1 | 4/2004 | Thornton |
| 2004/0226563 A1 | 11/2004 | Xu et al. |
| 2004/0237965 A1 | 12/2004 | Bibi et al. |
| 2005/0016544 A1 | 1/2005 | Thornton |
| 2005/0028827 A1 | 2/2005 | Halstrom |
| 2005/0034733 A1 | 2/2005 | Liddle et al. |
| 2005/0268914 A1 | 12/2005 | Paoluccio et al. ........ 128/205.25 |
| 2006/0005837 A1 | 1/2006 | Thornton |
| 2006/0124131 A1 | 6/2006 | Chandran et al. |
| 2007/0125388 A1 | 6/2007 | Thornton et al. |
| 2007/0235037 A1 | 10/2007 | Thornton ................. 128/848 |
| 2008/0006273 A1 | 1/2008 | Thornton |
| 2008/0006274 A1 | 1/2008 | Thornton |
| 2008/0032256 A1 | 2/2008 | Thornton |
| 2008/0127984 A1 | 6/2008 | Thornton ................. 128/848 |
| 2008/0295850 A1 | 12/2008 | Lesniak |
| 2009/0130624 A1 | 5/2009 | Sun et al. |
| 2010/0065067 A1 | 3/2010 | Lee |
| 2011/0168187 A1 | 7/2011 | Nelissen |

FOREIGN PATENT DOCUMENTS

| | | |
|---|---|---|
| DE | 2 320 501 | 11/1974 |
| DE | 35 43 931 A1 | 6/1987 |
| DE | 37 07 952 A1 | 9/1988 |
| DE | 37 19 009 A1 | 12/1988 |
| DE | 29506512.5 | 7/1995 |
| DE | 44 38 512 | 5/1996 |
| DE | 198 46 686 | 7/1999 |
| EP | 0 312 368 A1 | 4/1989 |
| EP | 0 359 135 A1 | 3/1990 |
| FR | 2 658 725 A1 | 8/1991 |
| FR | 2731624 | 9/1996 |
| GB | 1 569 129 | 6/1980 |
| GB | 2 072 567 A | 10/1981 |
| WO | WO 91/12777 | 9/1991 |
| WO | WO 97/25010 | 7/1997 |
| WO | WO 98/20924 | 5/1998 |
| WO | WO 98/26736 | 6/1998 |
| WO | WO 98/46177 | 10/1998 |

OTHER PUBLICATIONS

Photocopies of 2-piece dental device manufactured by Currie-Gibson Dental Lboratory, Inc., prior to Apr. 13, 1993, 5 pages.

Farrar, et al, *A Clinical Outline of Temporomandibular Joint Diagnosis and Treatment*, Normandie Study Group for TMJ Dysfunction, 3 pages, 1983.

Professional Positioners; *Dedicated to Excellence* brochure, 3 pages.

Great Lakes Orthodontics, Ltd.; *Nocturnal Airway Patency Applicance*; 2 pages.

Schmidt-Nowara, et al.; An American Sleep Disorders Association Review; *Oral Appliances for the Treatment of Snoring and Obstructive Sleep Apnea: A Review*; pp. 501-510, 1995.

George, Peter; *Treatment of Snoring and Obstructive Sleep Apnea with a Dental Device*; 5 pages, Jul.-Aug. 1993.

Database WOI, Section PQ, Week 9039, Derwent Publications, Ltd., London, GB; XP-002116355 Abstract—*Surgical Mouth Air Duct*; 1 page, Dec. 15, 1989.

PCT Notification of Transmittal of The International Search Report or the Declaration for International Application No. PCT/US97/08708, 4 pages, Aug. 12, 1997.

PCT Invitation to Pay Additional Fees for International Application No. PCT/US03/13705, 6 pages, Oct. 10, 2003.

PCT International Search Report and Written Opinion, International Application No. PCT/US06/26622, 11 pages, Feb. 21, 2007.

"Donning the Mask," Dräger: X-plore 5500.2006.Dräger Safety, http://www.draeger-usa.com/ST/internet/pdf/US/protection/AnlegiPO_X-plore_5500_US.pdf, 2 pages, Accessed Sep. 14, 2006.

PCT, Notification of Transmittal of the International Search Report and the Written Opinion of the International Searching Authority, or the Declaration, PCT/US07/02736, 10 pages, Date Mailed Oct. 26, 2007.

Thornton, "Oral Appliance for Treating a Breathing Condition," pending, U.S. Appl. No. 11/278,918, 42 pages, filed Apr. 6, 2006.

CPAP-PRO—Introducing a New Comfort Level for CPAP Users brochure, 2 pages.

W. Keith Thornton, "Multi-Chamber Mask and Method of Forming the Same," U.S. Appl. No. 11/428,933, filed Jul. 6, 2006.

W. Keith Thornton, "Improved Stability Medical Mask," currently pending, U.S. Appl. No. 11/853,343, filed Sep. 11, 2007.

W. Keith Thornton, "System and Method for Custom-Orienting a Medical Mask to an Oral Appliance," currently pending, U.S. Appl. No. 11/947,291, filed Nov. 29, 2007.

European Patent Office, Application No. 03 809 555.0-125, Applicant: W. Keith Thornton, 3 pages, dated Feb. 23, 2010; 4 pages, Aug. 7, 2009.

Canadian Intellectual Property Office, Application No. 2,502,280, Applicant: W. Keith Thornton, 3 pages, dated Feb. 23, 2010.

PCT, Notification of Transmittal of the International Search Report and the Written Opinion of the International Searching Authority, or the Declaration, International Application No. PCT/US2011/039231, filing date Jun. 6, 2011 (11 pgs), Mailing date Sep. 12, 2011.

Craig, William H., et al.; "Skeletal class II treatment with the Chateau appliance," The Journal of Pedondontics (vol. 11:120); pp. 120-138, 1987.

Samuel T. Kuna, M.D., et al., "Effect of Progressive Mandibular Advancement on Pharyngeal Airway Size in Anesthetized Adults," National Institute of Health; NIH Public Access Author Manuscript; Published Oct. 2008; Anesthesiology; 109(4); 16 pages, Oct. 2008.

Australian Office Action re: Pat. App. # 2007243957; dated Mar. 9, 2012; 3 pages, Mar. 9, 2012.

Acurest, The Logic Sleep Mask, http://sleepapneamasks.com.au/, 2002.

Whitestone et al., Fabrication of Total Contact Burn Masks Using Non-Contact Surface Scanning: A New Standard of Care, 1997, pp. 1-8, 1997.

Personally Moulded Sleep Apnea Masks, http:/;web.archive.org/web/20030618145716/ www.sleepapneamasks.com.au/default.asp, downloaded Aug. 17, 2009 (2 pages).

PCT, Notification of Transmittal of the International Search Report and the Written Opinion of the International Searching Authority, or the Declaration, PCT/US 2010/051136, 10 pages, Mar. 4, 2011.

Japanese Patent Office re patent application 2004-500750, mailed Oct. 14, 2008.

PCT Intl. Searching Authority, Invitation to pay Add'l Fees, Re PCT/US2012/028885 mailed May 30, 2012 (0306 Foreign).

PCT Intl. Searching Authority, Invitation to pay Add'l Fees, Re PCT/US2012/032407 mailed May 30, 2012.

SYSTEM FOR COUPLING AN ORAL APPLIANCE TO A MEDICAL MASK

RELATED APPLICATIONS

This application claims the benefit under 35 U.S.C. §120 as a continuation-in-part of Ser. No. 11/278,918, now U.S. Pat. No. 7,748,386 filed Apr. 6, 2006, which is incorporated herein by reference.

TECHNICAL FIELD OF THE INVENTION

This invention relates generally to oral appliances, and more particularly to an oral appliance for use in treating a breathing condition.

BACKGROUND

Many people experience breathing problems, which may result in difficulty sleeping, in snoring, or in other more serious conditions such as obstructive sleep apnea. One treatment for such breathing disorders involves the use of devices that are inserted into a user's mouth for extending the user's lower jaw forward. These devices open the airway (i.e., breathing passageway) more fully to allow easier breathing through the nose and mouth. Certain of these devices include upper and lower arches that are connected together using a mechanism that may be adjusted to pull the lower arch, and thus the user's lower jaw, forward to open the airway more fully.

Another treatment for breathing disorders involves application of continuous positive air pressure ("CPAP") to the patient. The CPAP is delivered through a face mask, nose mask, or nasal inserts, and results in a fuller opening of the patient's breathing passageway. The CPAP may be increased for more serious conditions. Face masks for delivering CPAP are commonly secured to the patient's head with a strap that wraps around the user's head. As the patient moves, the face mask often shifts and unseats from the patient's face, which may reduce the CPAP or awaken a sleeping patient.

SUMMARY OF THE INVENTION

Oral appliances and methods according to the present invention may reduce or eliminate certain disadvantages and problems associated with previous devices and methods for improving breathing.

In certain embodiments, an apparatus for treating a breathing condition includes an oral appliance, a mask, and a tensioning device. The oral appliance is configured to receive at least some of a wearer's teeth and a mask. The mask is configured to deliver gas to the wearer. The mask includes a chamber configured to cover the wearer's mouth. The chamber is at least partially enclosed by an interior of the mask. The tensioning device couples the mask to the oral appliance and includes a flexible tension element at least partially disposed between the oral appliance and the mask and within the chamber. The flexible tension element is configured to apply a tensile force between the mask and the oral appliance.

Certain embodiments of the present invention may provide one or more technical advantages. For example, particular embodiments may adjustably tighten and optimally position a gas delivery system against a user's face without the use of elements that wrap around the user's head. In addition, certain embodiments may be configured to adjustably reposition a gas delivery system along multiple axes. Various embodiments may absorb forces caused by the movement of a gas delivery system and may minimize the transfer of such forces to the user. Particular embodiments may be configured to automatically redistribute forces along surfaces where a gas delivery system comes in contact with a user's face. Certain embodiments may provide some, none, or all of these advantages. Certain embodiments may provide one or more other technical advantages, one or more of which may be readily apparent to those skilled in the art from the figures, description, and claims included herein.

BRIEF DESCRIPTION OF THE DRAWINGS

For a more complete understanding of the present invention and at least some of its advantages, reference is now made to the following description taken in conjunction with the accompanying drawings, in which.

DESCRIPTION OF EXAMPLE EMBODIMENTS

Figure 1:
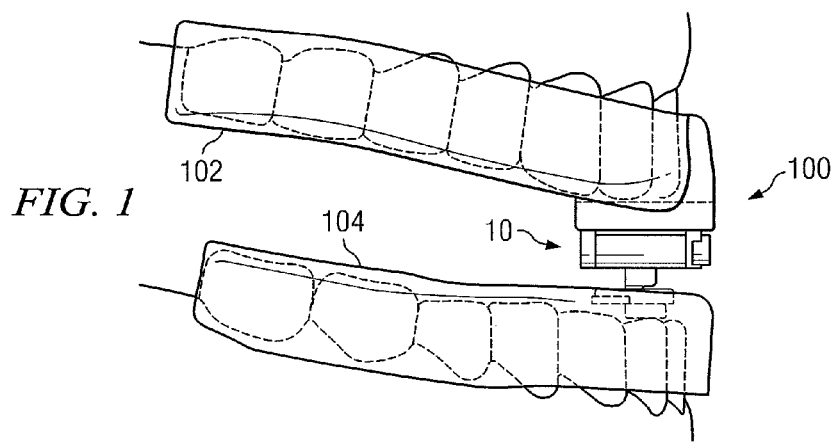
FIG. 1 illustrates an example oral appliance for improving a user's breathing.
Figure 2A:
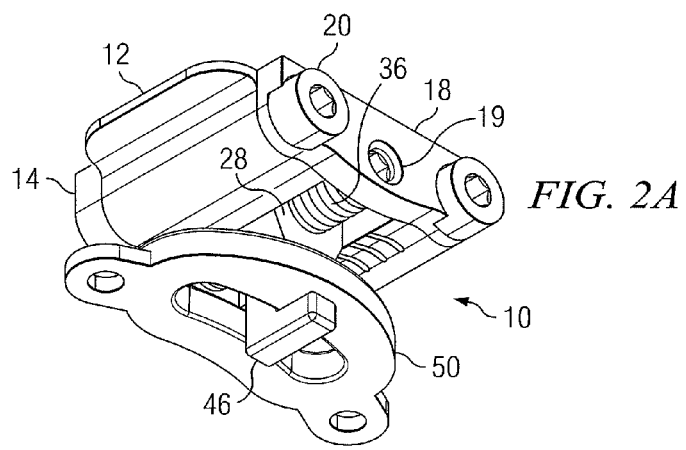
FIGS. 2A through 5B illustrate an example adjustment mechanism.
Figure 2B:
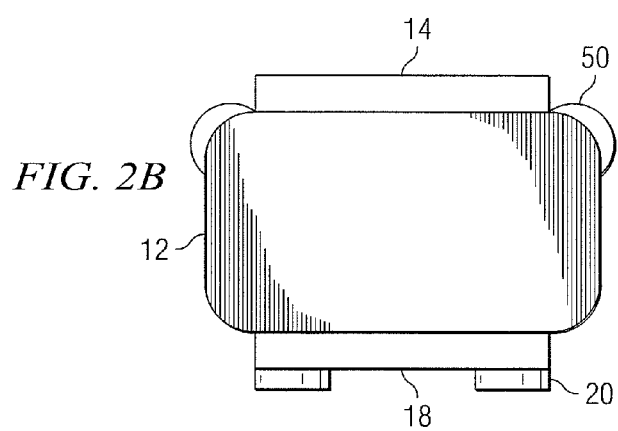
Figure 2C:
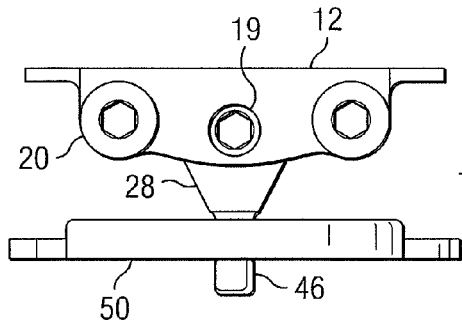
Figure 2D:
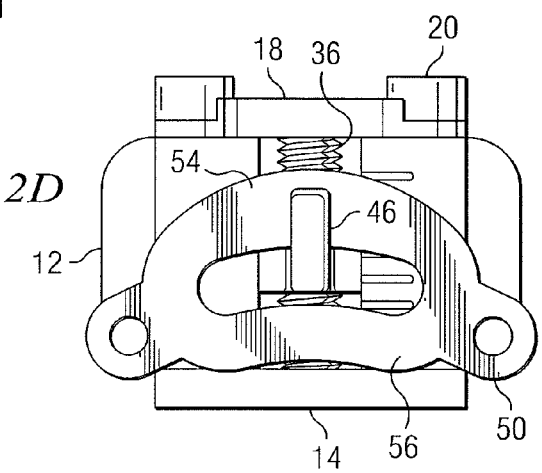
Figure 3:
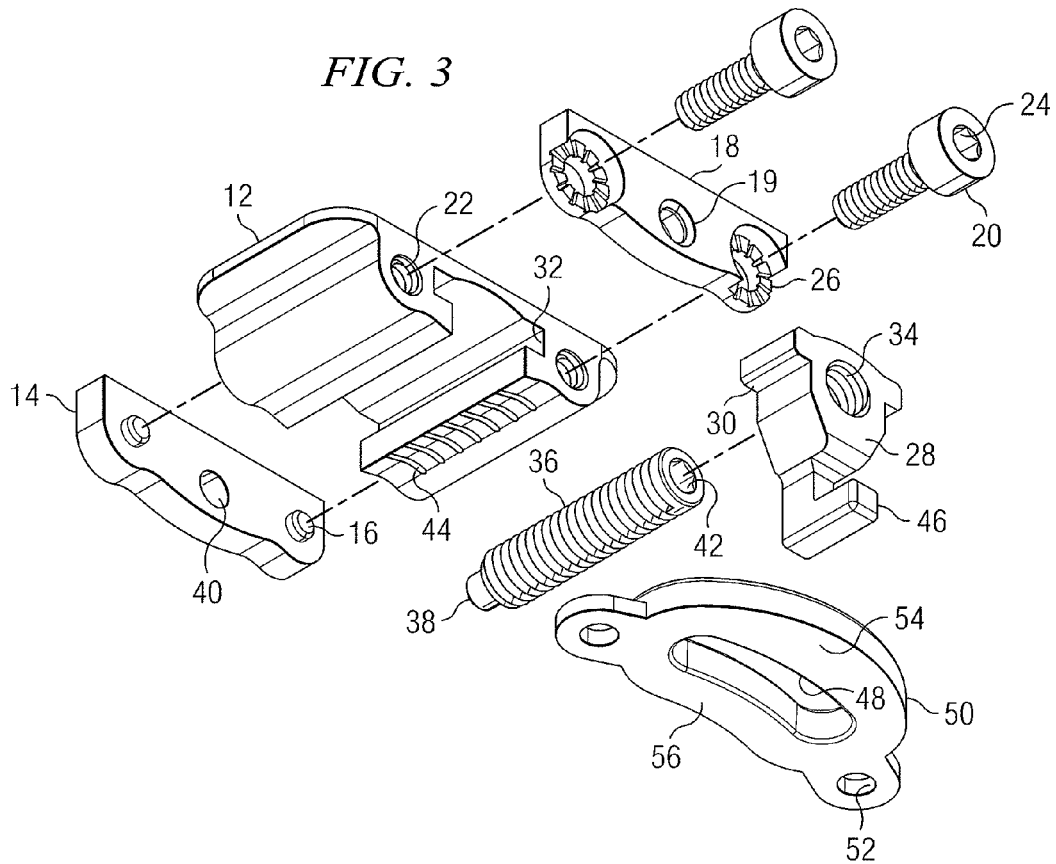
Figure 4A:
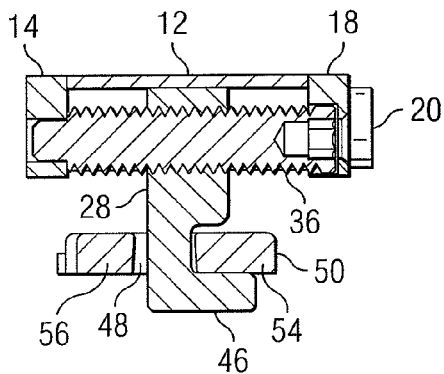
Figure 4B:
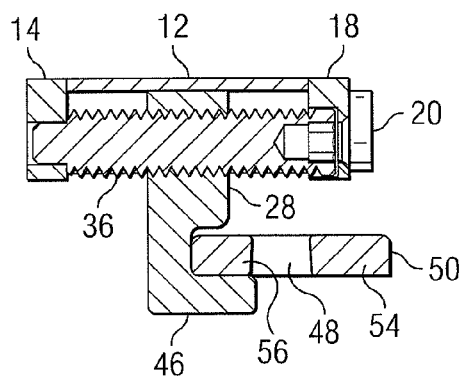
Figure 5A:
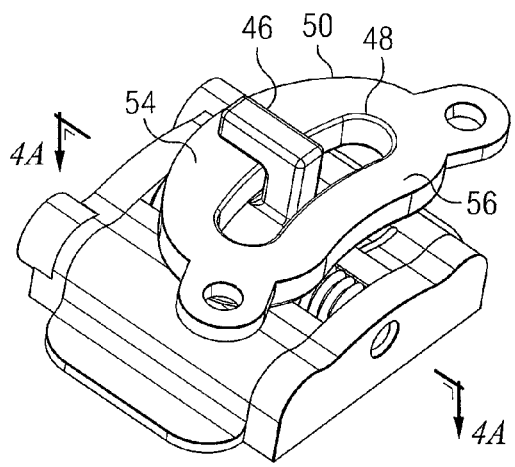
Figure 5B:
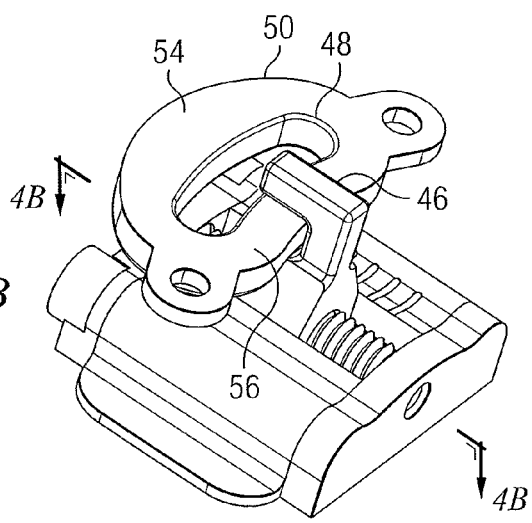

FIG. 1 illustrates an example oral appliance 100 for improving a user's breathing. In general, oral appliance 100 may be used to treat sleep disordered breathing, such as snoring or obstructive sleep apnea, through forward adjustment of the user's lower jaw relative to the upper jaw. This forward adjustment opens the breathing passage more fully and facilitates improved breathing through the user's nose and mouth. In certain embodiments, oral appliance 100 remains entirely within the user's mouth and surfaces of oral appliance 100 that may contact the interior of the user's mouth are smooth to prevent injury or discomfort. Although not intended to be exclusive, example oral appliances are described in one or more of U.S. Pat. Nos. 5,427,117; 5,566, 683; 5,755,219; 6,516,805; 5,954,048; 5,983,892; 6,374,824; 6,325,064; 6,247,926; and 6,405,729, each of which is incorporated herein by reference.

Oral appliance 100 includes an upper arch 102 configured to receive at least some of a user's upper teeth, a lower arch 104 configured to receive at least some of the user's lower teeth, and an adjustment mechanism 10. Upper arch 102 and lower arch 104 may include molds of at least some of the user's upper and lower teeth, respectively, for improved performance and comfort. Adjustment mechanism 10 couples lower arch 104 to upper arch 102 and may be adjusted to pull lower arch 104 forward to facilitate improved breathing. In certain embodiments, adjustment mechanism 10 may also vertically position lower arch 104 relative to upper arch 102 to determine the opening of the user's lower jaw. The components of adjustment mechanism 10 may be made from any suitable material such as, for example, a biocompatible metal or hard plastic.

FIGS. 2A through 5B illustrate an example adjustment mechanism 10 for use with oral appliance 100. In certain embodiments, adjustment mechanism 10 may include body 12, hook 28, adjustor 36, and receiver 50. Body 12 may be integrated into or coupled to upper arch 102. Body 12 may include a rear plate 14, one or more rear fasteners 16, a front plate 18, and one or more front fasteners 20. In certain embodiments, body 12 may further include one or more fastener passages 22, one or more guides 32, and one or more adjustment indicators 44. Hook 28 may include flange 30, adjustor passage 34, and arm 46.

When assembled, rear plate 14 may be coupled to body 12 through the use of one or more fasteners 16. Fasteners 16 may be threaded fasteners, pins, or any other appropriate fastener to couple rear plate 14 to body 12. Hook 28 may be coupled to body 12 through the use of one or more flanges 30 engaged within the one or more guides 32. Adjustor 36 may include pin 38 and opening 42. Opening 42 may be square, hexagonal, or any other appropriate shape to allow for a rotational force to be applied to adjustor 36. Adjustor 36 may be positioned within adjustor passage 34 of hook 28 and pin 38 may be aligned with and inserted into hole 40 of rear plate 14. Front plate 18 may be coupled to body 12 through the use of one or more fasteners 20. Fasteners 20 may include threaded fasteners, pins, or any other appropriate fastener to couple front plate 18 to body 12. In certain embodiments, front plate 18 may include one or more structures to lock or secure one or more fasteners 20. For example, in embodiments utilizing a threaded fastener 20 as shown, front plate 18 may include one or more grooves and associated projections 26 to better secure fastener 20 in place.

In certain embodiments, front plate 18 may include an opening 19 that substantially aligns with opening 42 of adjustor 36. In operation, opening 19 may provide access to opening 42 of adjustor 36 for locational adjustment of hook 28. In certain embodiments, adjustor 36 may be threaded and may engage cooperative threads of adjustor passage 34 of hook 28 such that rotation of adjustor 36 moves hook 28 forward or rearward relative to body 12.

Receiver 50 is configured to receive arm 46 of hook 28 such that forward adjustment of hook 28 pulls lower arch 104 forward. Receiver 50 may be fully integrated into, permanently coupled to, or separate and removable from lower arch 104. In certain embodiments, receiver 50 may include one or more openings 52 that may be used to couple receiver 50 to lower arch 104 through the use of any appropriate fastener. In certain embodiments, receiver 50 may also include slot 48 separating front shelf 54 from rear shelf 56. In operation, hook 28 may engage either front shelf 54 or rear shelf 56. In certain embodiments, the use of rear shelf 56 may provide additional extension of lower arch 104 in the forward direction relative to the use of front shelf 54.

Receiver 50 may be modified according to particular needs to provide increased flexibility. For example, the vertical location of front shelf 54 and/or rear shelf 56 relative to lower arch 104 may be adjusted or otherwise modified, either during or after initial construction of receiver 50. As another example, receivers 50 with varying vertical dimensions may be provided, such that the use of a particular receiver 50 may be selected to define a prescribed vertical separation between upper arch 102 and lower arch 104 and thus a prescribed opening of the user's lower jaw. As another example, the vertical location of front shelf 54 and/or rear shelf 56 may be selected by coupling receiver 50 to lower arch 104 in either of two possible orientations (i.e., with a particular horizontal surface facing up or facing down). As another example, receivers 50 with varying horizontal dimensions may be provided, such that the use of a particular receiver 50 may be selected to define a prescribed forward location (or range of locations) for lower arch 104 relative to upper arch 102.

Slot 48 may allow horizontal movement of lower arch 104 relative to lower upper 102 when lower arch 104 is coupled to upper arch 102. Similarly, the posterior surface of front shelf 54 and/or rear shelf 56 may be shaped to guide the horizontal movement of lower arch 104 relative to upper arch 102 in an arc-shaped or other desirable path.

Figure 6A:
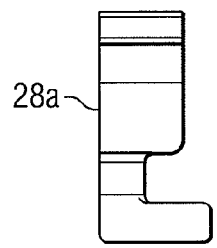
FIGS. 6A through 6C illustrate example hooks with varying lengths, for use with an example adjustment mechanism.
Figure 6B:
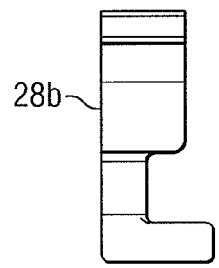
Figure 6C:
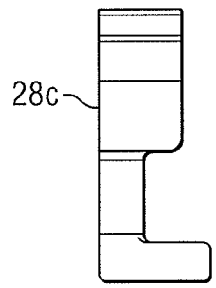

FIGS. 6A through 6C illustrate example hooks 28 with varying lengths, for use with adjustment mechanism 10. In operation, the use of a particular hook 28 may be selected to define a prescribed vertical separation between upper arch 102 and lower arch 104 and thus a prescribed opening of the user's lower jaw. For example, in the embodiments shown, the use of hook 28c may allow for greater vertical separation between upper arch 102 and lower arch 104 than the vertical separation allowed with the use of hooks 28a or 28b. In particular embodiments, the use of hooks 28 with varying lengths, together with the use of receivers 50 with varying vertical dimensions, may provide an increased range and/or precision for selection of a prescribed opening of the user's lower jaw.

Figure 7A:
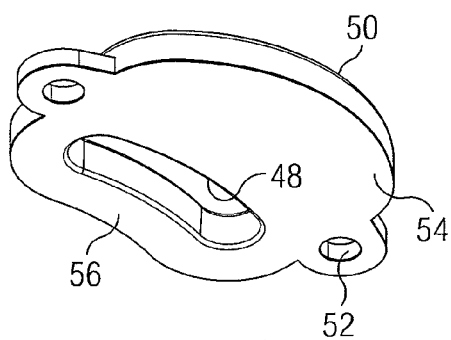
FIGS. 7A through 7C illustrate example receivers with varying dimensions.
Figure 7B:
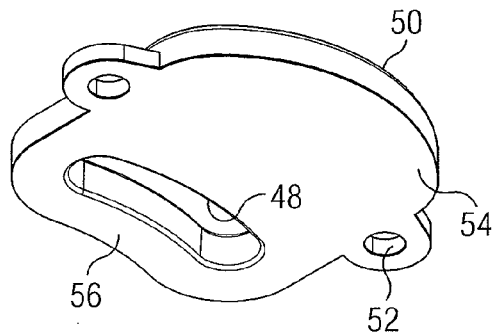
Figure 7C:
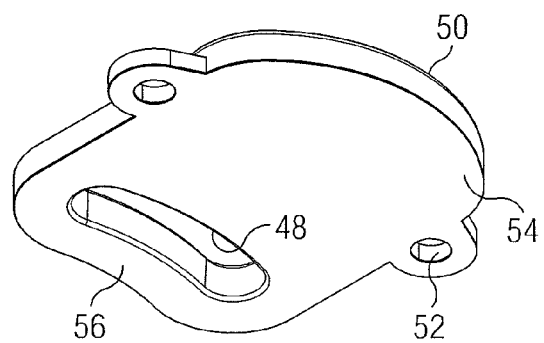
Figure 8A:
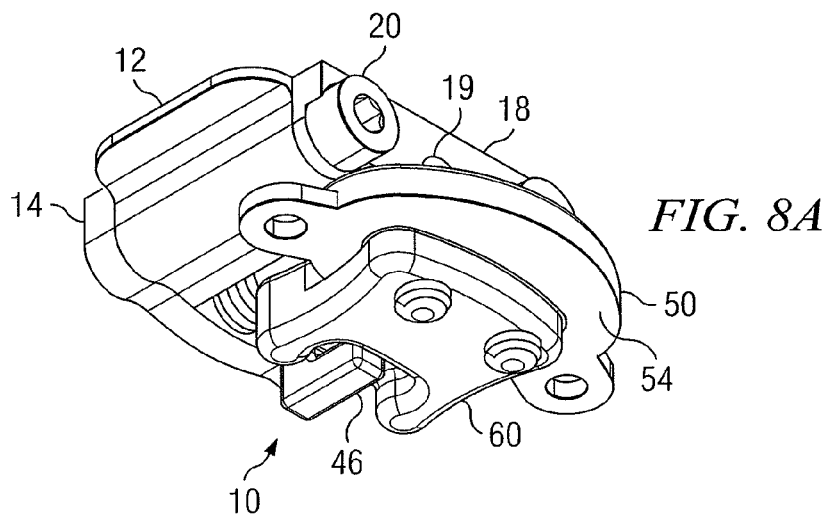
FIGS. 8A through 10 illustrate an example adjustment mechanism utilizing an example extender.
Figure 8B:
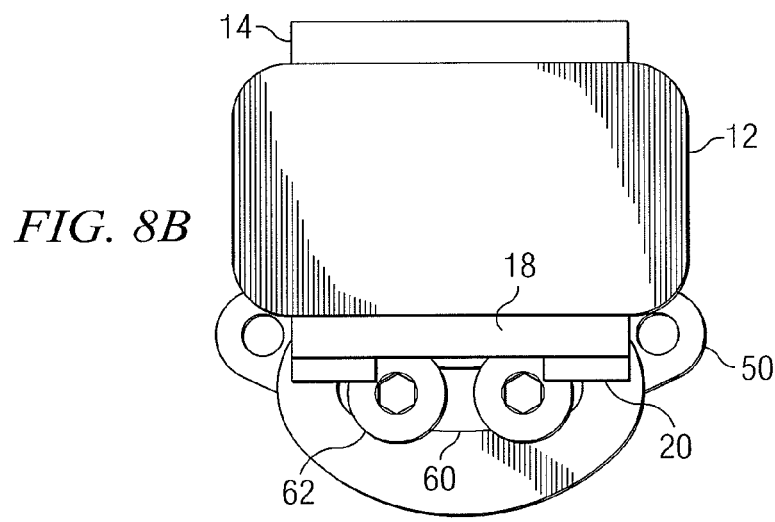
Figure 8C:
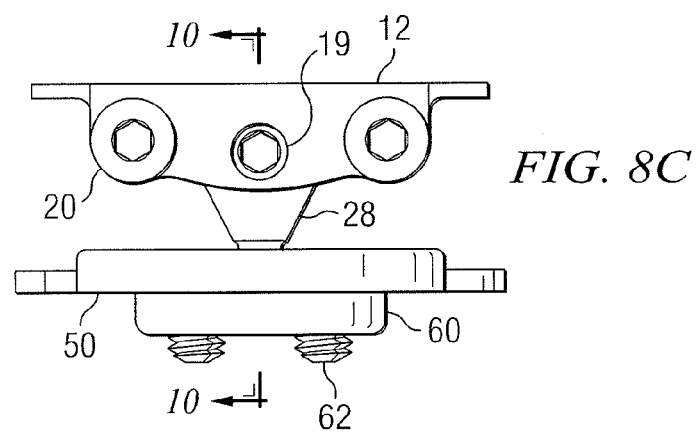
Figure 8D:
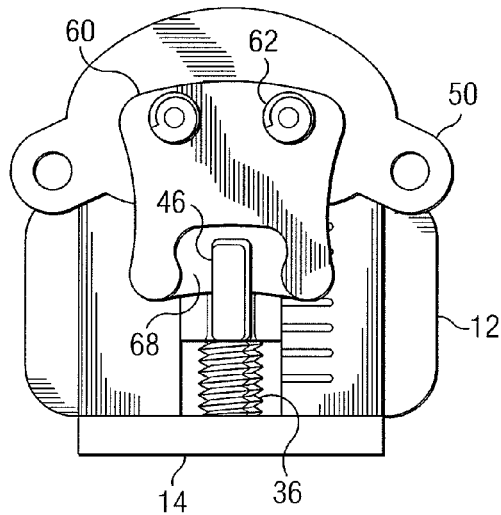
Figure 9:
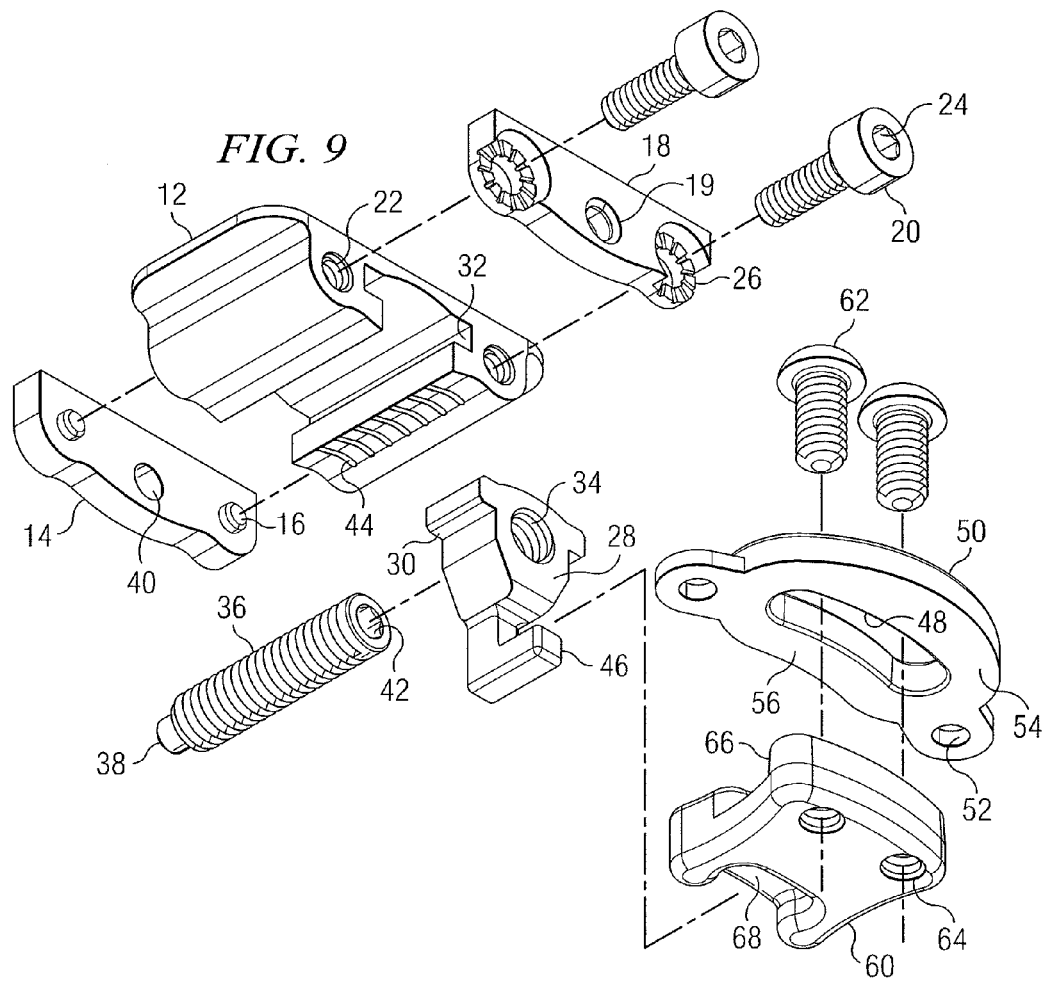
Figure 10:
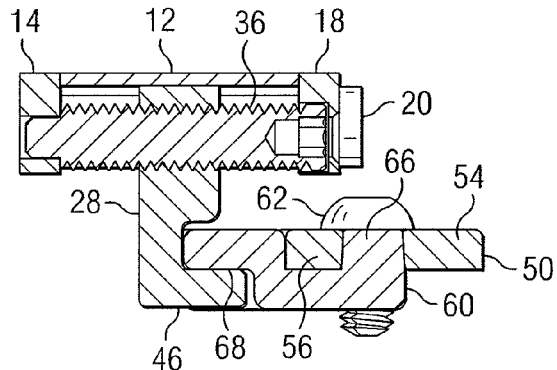

FIGS. 7A through 7C illustrate example receivers with varying dimensions, for use with adjustment mechanism 10. In operation, the use of a particular receiver may be selected to define a prescribed forward location (or range of forward locations) for lower arch 104 relative to upper arch 102 and thus a prescribed forward location (or range of forward locations) for the user's lower jaw. For example, in the embodiments shown, the use of receiver 50c may allow for lower arch 104 to be positioned further forward with respect to upper arch 102 than with the use of receivers 50a or 50b. In particular embodiments, the use of receivers 50 with varying dimensions may provide an increased range and/or precision for adjusting the forward location of lower arch 104 relative to upper arch 102.

FIGS. 8A through 10 illustrate an example adjustment mechanism 10 utilizing an example extender 60. In certain embodiments, extender 60 couples to receiver 50 and operates to receive arm 46 of hook 28 such that the forward positioning of lower arch 104 is greater than that provided without extender 60.

Figure 11A:
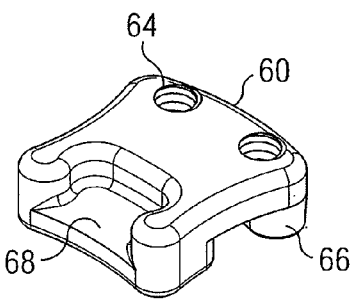
FIGS. 11A and 11B illustrate an example extender.
Figure 11B:
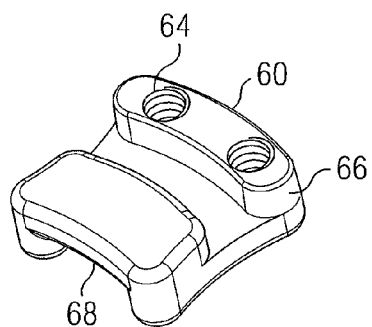

FIGS. 11A and 11B illustrate an example extender 60 for use with an example adjustment mechanism 10. In certain embodiments, extender 60 may include a shelf 68 that engages arm 46 of hook 28. In certain embodiments, extender 60 may also include one or more projections 66 that may cooperatively engage slot 48 of receiver 50. In certain embodiments, extender 60 may also include one or more openings 64 that may cooperate with one or more fasteners 62 to couple extender 60 to receiver 50, such as via slot 48. Fastener 62 may be a threaded fastener, pin, or any other appropriate fastener for coupling extender 60 to receiver 50.

Figure 12A:
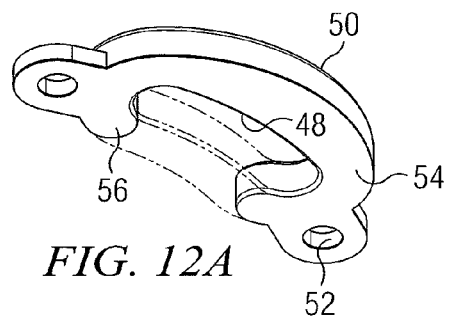
FIGS. 12A and 12B illustrate example receivers.
Figure 12B:
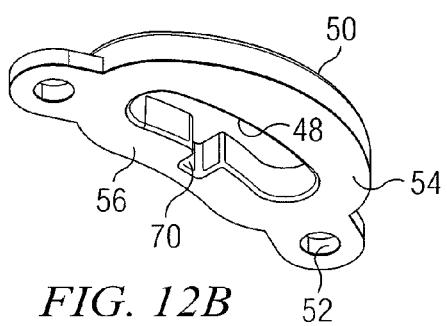

FIGS. 12A and 12B illustrate example receivers 50 for use with example adjustment mechanisms 10. As shown in FIG. 12A, in certain embodiments, receiver 50 may include only a single shelf 54, in which case slot 48 may be fully or partially exposed in the rearward direction. As shown in FIG. 12B, receiver 50 may include notch 70 in slot 48. In operation, the use of receiver 50 including only a single shelf 54 or including notch 70 may allow hook 28 to engage or disengage from shelf 54 of receiver 50 after oral appliance 100 has been inserted into a user's mouth.

Figure 13:
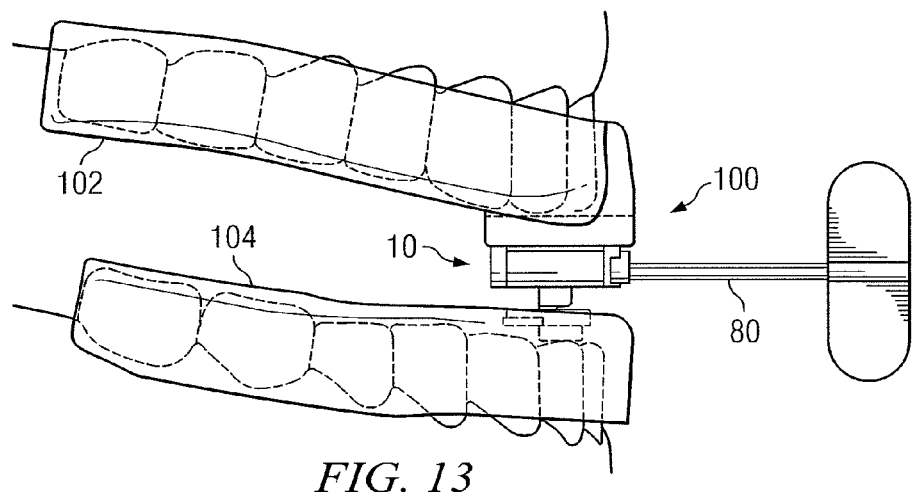
FIGS. 13 through 16 illustrate an example adjustment mechanism utilizing an example adjustment key.

FIG. 13 illustrates an example oral appliance 100 with an example adjustment key 80. Adjustment key 80 may have a cross-section that is hexagonal, square, or any other appropriate shape. In certain embodiments, adjustment key 80 may be used to exert a rotational force on adjustor 36 causing adjustor 36 to turn and thereby provide adjustment of hook 28, forward or rearward.

Figure 15:
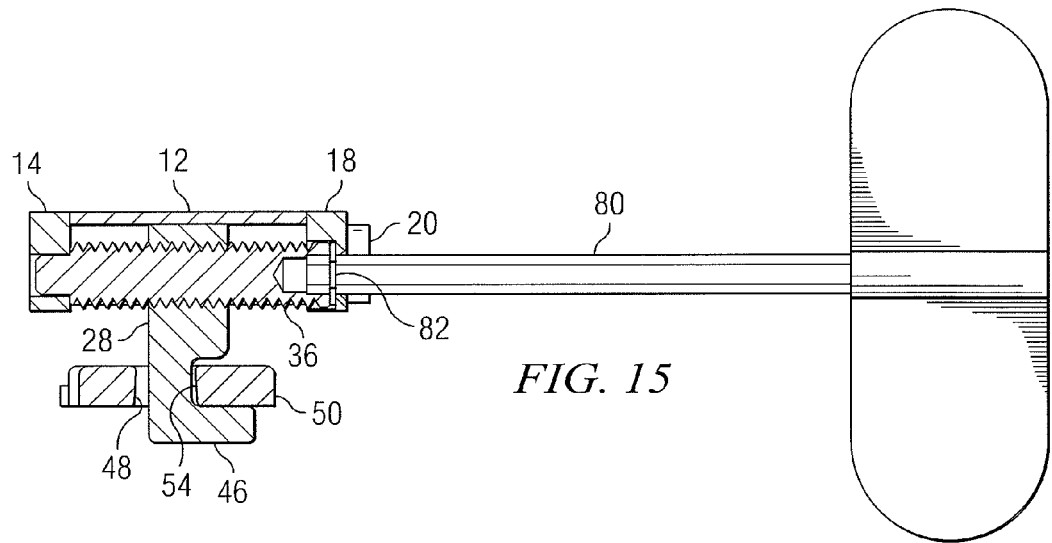
Figure 14:
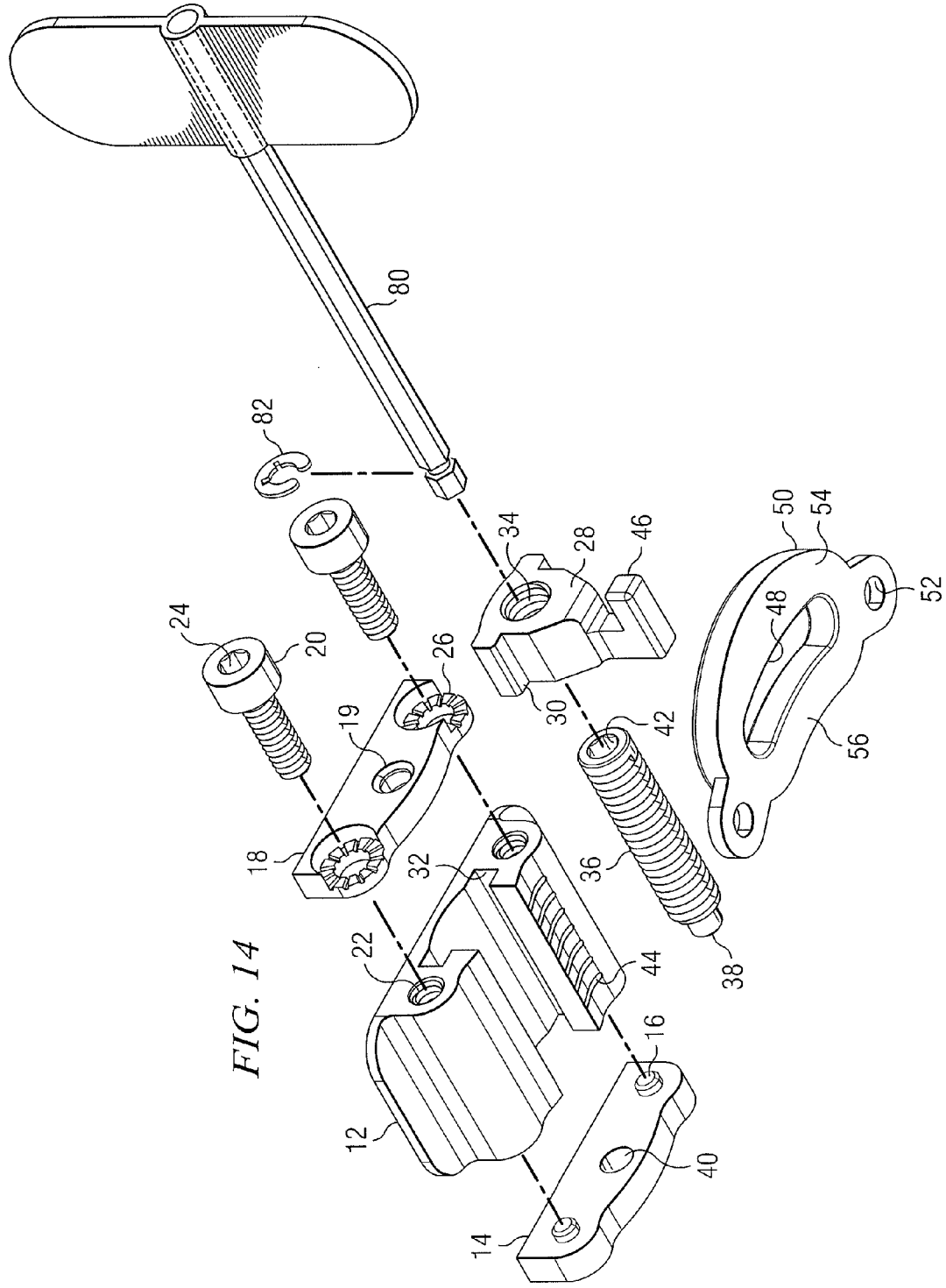
Figure 16:
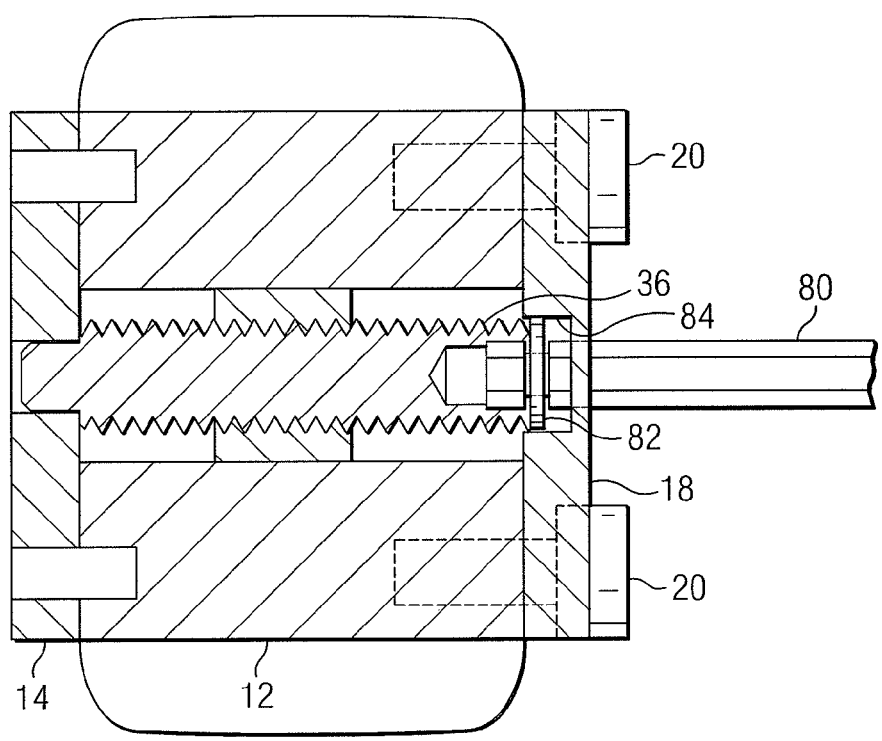
Figure 17:
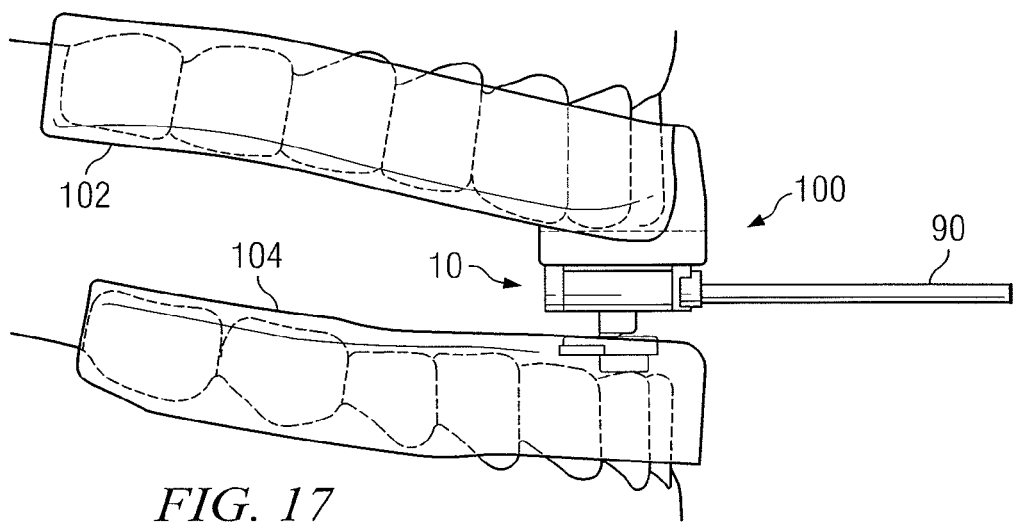
FIGS. 17 through 19B illustrate an example adjustment mechanism utilizing an example extension post.
Figure 18:
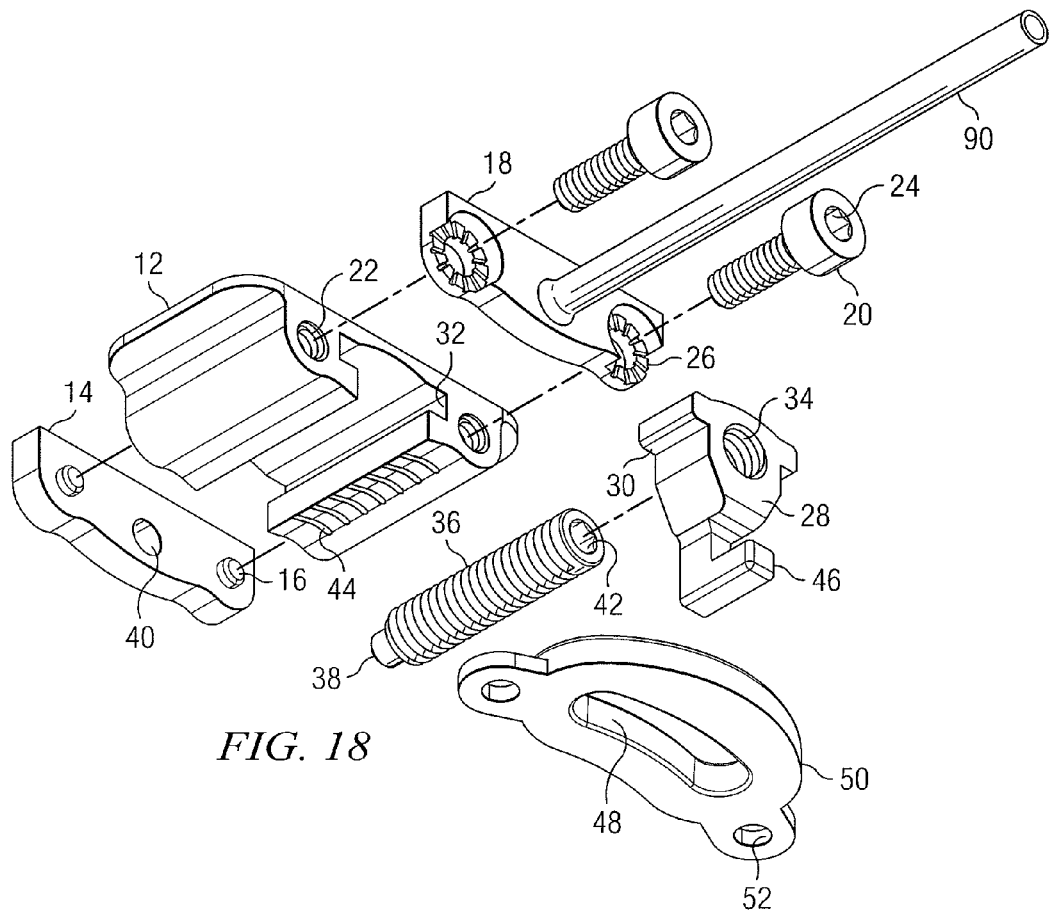

FIGS. 14 through 16 illustrate example adjustment mechanisms 10 utilizing example adjustment keys 80. In certain embodiments, adjustment key 80 may be coupled to adjustment mechanism 10 through the use of retainer ring 82 and notch 84. In operation, retainer ring 82 may engage notch 84, thus preventing removal of adjustment key 80. In operation, embodiments of adjustment mechanism 10 including adjustment key 80 and retaining ring 82 may be used by a particular user during a trial period for oral appliance 100. During this trial period, the user and/or a clinician may make periodic adjustments to adjustment mechanism 10 through the use of adjustment key 80 to achieve the desired positioning of lower arch 104 relative to upper arch 102. In these embodiments, once the desired positioning has been achieved, adjustment key 80 and retaining ring 82 may be removed. In these embodiments, once the desired positioning has been achieved, front plate 18 may be replaced with a front plate 18 that does not include an opening 19.

FIGS. 17 through 19B illustrate an example oral appliance 100 with an example extension post 90. Extension post 90 may be formed of any suitable material, such as a metal or hard plastic. In certain embodiments, extension post 90 may be used to couple oral appliance 100 to one or more other devices and/or to orient one or more other devices relative to oral appliance 100. For example, extension post 90 may be used to couple oral appliance 100 to a breathing device, such as a venting seal, a face mask, or a nose mask. In a particular embodiment, extension post may be used to couple oral appliance 100 to a mask associated with a continuous positive airway pressure (CPAP) system.

In certain embodiments, extension post 90 may be substantially rigid, to provide for sufficiently precise positioning of one or more devices relative to upper arch 102. For example, in certain embodiments, extension post 90 may be used to provide substantially precise and repeatable positioning of a face mask or nose mask relative to upper arch 102. The length of extension post 90 may vary depending upon its intended use. For example, extension post 90 may be substantially shorter if it is intended to be used to couple a venting seal to oral appliance 100 than if it is intended to couple a nose mask to oral appliance 100. The invention contemplates any reasonable length of extension post 90, so long as the length is appropriate to perform the intended function.

Figure 19A:
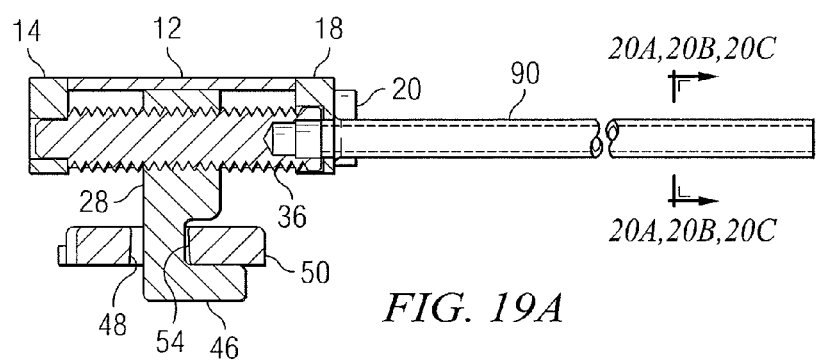
Figure 19B:
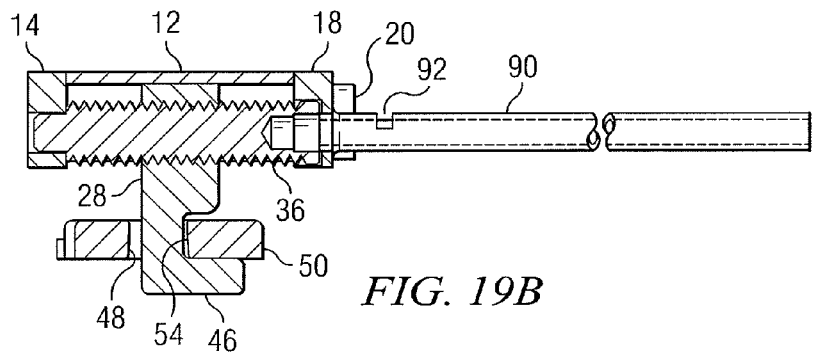

In certain embodiments, extension post 90 may include one or more features that can operate to index or assist in securing one or more devices to extension post 90. For example, as shown in FIG. 19B, extension post 90 may include one or more locators 92 at one or more positions along the length of extension post 90. In operation, a device coupled to or guided by extension post 90 may include one or more structures that can cooperate with the one or more locators 92 to index or assist in securing the device. In the embodiment shown, locator 92 is in the form of a notch, however, in alternative embodiments, locator 92 may be in the form of a ridge, protrusion, or any other appropriate shape or structure. In particular embodiments, the position of locator 92 may be adjustable.

In certain embodiments, extension post 90 may be coupled to front plate 18. In these embodiments, extension post 90 may be coupled through the use of any appropriate means, such as welding or threaded coupling. In alternative embodiments, extension post 90 may be integrally formed with front plate 18. In certain embodiments, extension post 90 may be substantially hollow and may couple to front plate 18 such that the hollow interior of extension post 90 substantially aligns with an opening 19. In operation, hollow portion 92 may provide access to adjustor 36 through opening 19. The cross-sectional shape of extension post 90 may take any appropriate form, so long as it remains reasonable for the intended function.

Figure 20A:
FIGS. 20A through 20B illustrate transverse cross-sectional views of example extension posts.
Figure 20B:
Figure 20C:

FIGS. 20A through 20C illustrate transverse cross-sectional views of example extension posts 90. As shown, extension post 90 may have a cross sectional shape that is a circle, oval, or diamond. In certain embodiments, non-circular cross-sections may function to more precisely position a device coupled to oral-appliance 100 through the use of extension post 90, by substantially limiting the likelihood that the device will rotate about the extension post 90.

In certain embodiments, receiver 50 may be removable. For example, lower arch 104 may include a recess that allows receiver 50 to be positioned within, and then removed from, lower arch 104. In embodiments including a removable receiver 50 and a recess in lower arch 104, the recess may be integrally formed in lower arch 104. In alternative embodiments, the recess may be formed in or by a housing that is included in lower arch 104.

Figure 21:
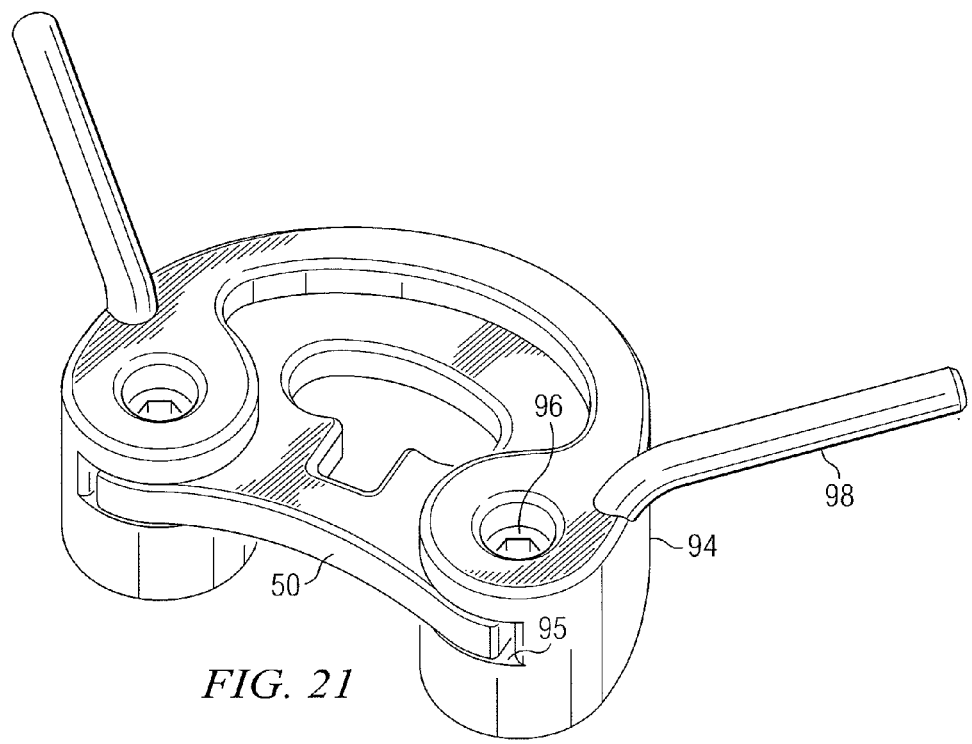
FIGS. 21 through 23 illustrate an example housing, for use with an example adjustment mechanism.
Figure 22:
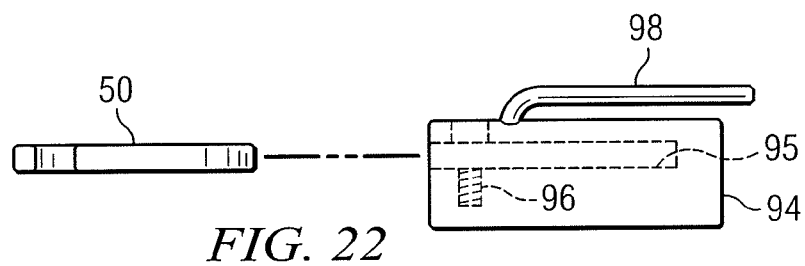
Figure 23:
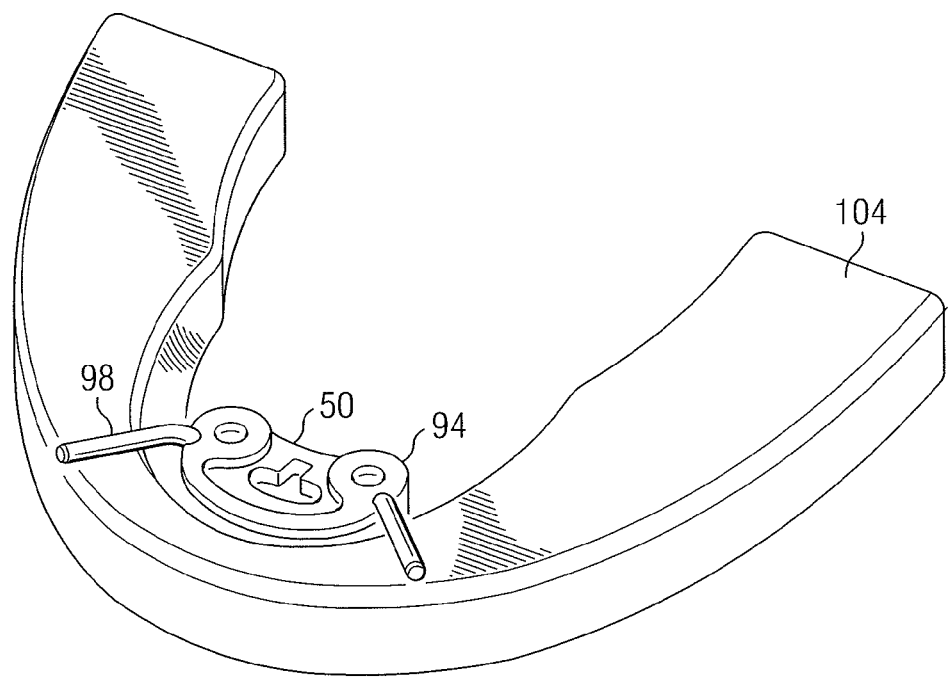

FIGS. 21 through 23 illustrate an example housing 94, for use with an example adjustment mechanism 10. In certain embodiments, adjustment mechanism 10 may include housing 94 to position and secure receiver 50. Housing 94 may be made of any appropriate material, such as metal or hard plastic. In certain embodiments, housing 94 may be integrally formed with lower arch 104. As shown, housing 94 may define recess 95 to accept receiver 50 within housing 94. In certain embodiments, housing 94 may include one or more fasteners 96 to secure receiver 50 within recess 95. In a particular embodiment, fastener 96 may be a threaded set-screw.

In certain embodiments, housing 94 may include one or more projections 98 that may be used to orient and/or secure housing 94 to lower arch 104. In particular embodiments, as in the example shown in FIG. 23, one or more projections 98 may be used to orient housing 94 to lower arch 104. In these embodiments, once housing 94 is properly oriented, housing 94 may be luted to (or otherwise secured to) lower arch 104. In certain embodiments, some or all of projections 98 may be removed before or after housing 94 is completely secured to lower arch 104.

FIGS. 24A through 25C illustrate example receivers 50, for use with an example housing 94. As shown, receiver 50 may have varying dimensions and the location of certain features of receiver 50 may vary. In operation, the use of a particular receiver 50 may be selected to define a prescribed forward location (or range of locations) for lower arch 104 relative to upper arch 102. For example, in the embodiments shown, the use of receiver 50f may allow for lower arch 104 to be positioned further forward with respect to upper arch 102 than with the use of receivers 50d and 50e. In particular embodiments, the use of receivers 50 with varying dimensions may provide an increased range and/or precision for adjusting the forward location of lower arch 104 relative to upper arch 102.

Figure 24A:
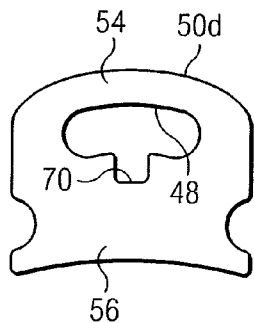
FIGS. 24A through 25C illustrate example receivers, for use with an example housing.
Figure 24B:
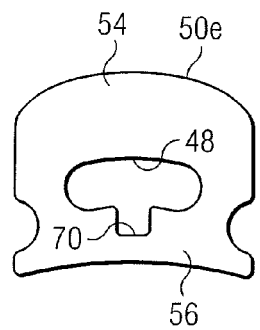
Figure 24C:
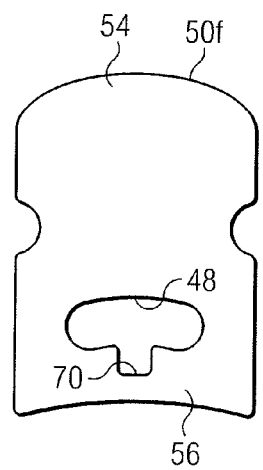
Figure 24D:
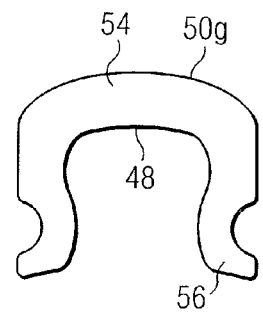

As shown in FIG. 24D, in certain embodiments, receiver 50 may include only a single shelf 54, in which case slot 48 may be fully or partially exposed in the rearward direction. In operation, the use of receiver 50 including only a single shelf 54 (or including notch 70) may allow hook 28 to engage or disengage from shelf 54 of receiver 50 after oral appliance 100 has been inserted into a user's mouth.

Figure 25A:
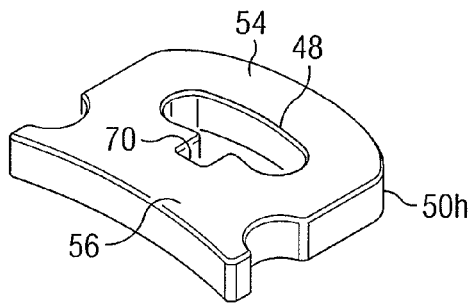
Figure 25B:
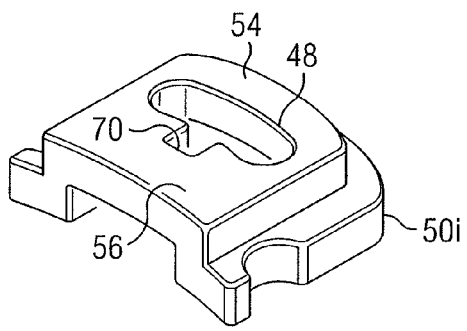
Figure 25C:
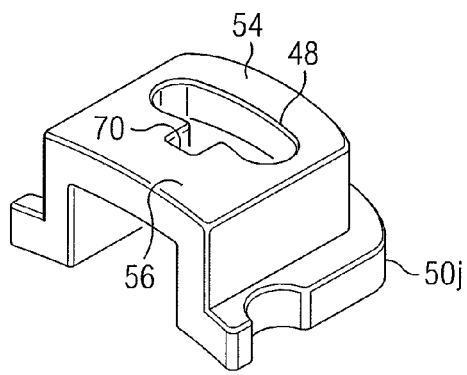

As shown in FIGS. 25A through 25C, receiver may have varying vertical dimensions. In operation, the use of a particular receiver 50 may be selected to define a prescribed vertical separation between upper arch 102 and lower arch 104 and thus a prescribed opening of the user's lower jaw. For example, in the embodiments shown, the use of receiver 50j may allow for greater vertical separation between upper arch 102 and lower arch 104 than the vertical separation allowed with the use of receivers 50h and 50i. In particular embodiments, the use of receivers 50 with varying vertical dimensions may provide an increased range and/or precision for selection of a prescribed opening of the user's lower jaw.

Figure 26:
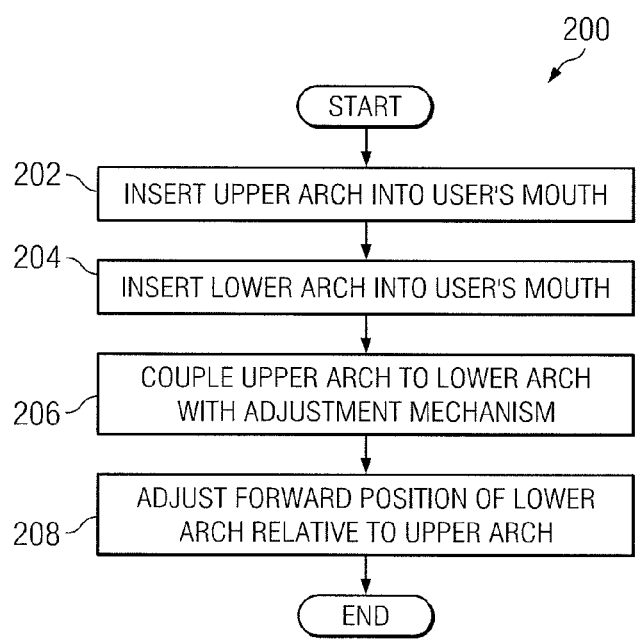
FIG. 26 illustrates an example method of improving a user's breathing.

FIG. 26 illustrates an example method of improving a user's breathing, indicated generally at 200. At step 202, upper arch 102 is inserted into the user's mouth. At step 204, lower arch is inserted into the user's mouth. At step 206, upper arch 102 is coupled to lower arch 104 by adjustment mechanism 10. In certain embodiments, adjustment mechanism 10 includes a body 12 coupled to upper arch 102, an adjustor 36, a hook 28, and a receiver 50 coupled to lower arch 104. In certain embodiments, upper arch 102 is coupled to lower arch 104 by engaging shelf 54 of receiver 50 with arm 46 of hook 28. In particular embodiments, the initial forward position of lower arch 104 relative to upper arch 102 is determined by engaging a particular one of multiple shelves 54 of receiver 50. In alternative embodiments, the initial forward position of lower arch 104 relative to upper arch 102 is determined by engaging shelf 68 of extender 60 coupled to receiver 50. At step 208, the forward position of lower arch 104 relative to upper arch 102 is adjusted to facilitate improved breathing by the user. In certain embodiments, the forward position is adjusted by rotating adjustor 36 using adjustment key 80 or in any other appropriate manner.

Although an example method is described, the steps may be accomplished in any appropriate order. For example, inserting the upper and lower arches can be accomplished sequentially, in any order, or simultaneously. As another example, upper arch 102 and lower arch 104 may be coupled subsequent to or prior to inserting upper arch 102 and lower arch 104 into the user's mouth. As another example, the adjustment of the forward position of lower arch 104 relative to upper arch 102 may be performed in measured increments interspersed with trial periods to test the effectiveness of the oral appliance in improving the user's breathing. Method 200 may include checking or verifying the forward position of lower arch 104 relative to upper arch 102 and then repeating step 208 as needed. The present invention contemplates using methods with additional steps, fewer steps, or different steps, so long as the methods remain appropriate for improving a user's breathing.

FIGS. 27A through 27D illustrate an example oral appliance 500 configured to cooperate with a flexible tension element 510 to adjustably position a mask 522 of a gas delivery system 520 against a user's face. In particular embodiments, oral appliance 500, flexible tension element 510, and gas delivery system 520 cooperate together to improve a user's breathing. In certain embodiments, oral appliance 500 may provide functionality substantially similar to oral appliance 100 of FIG. 1, though oral appliance 500 may provide other functionality different from that provided by oral appliance 100. Particular embodiments of oral appliance 500 may be substantially different in structure from oral appliance 100, as explained further below.

Figure 27A:
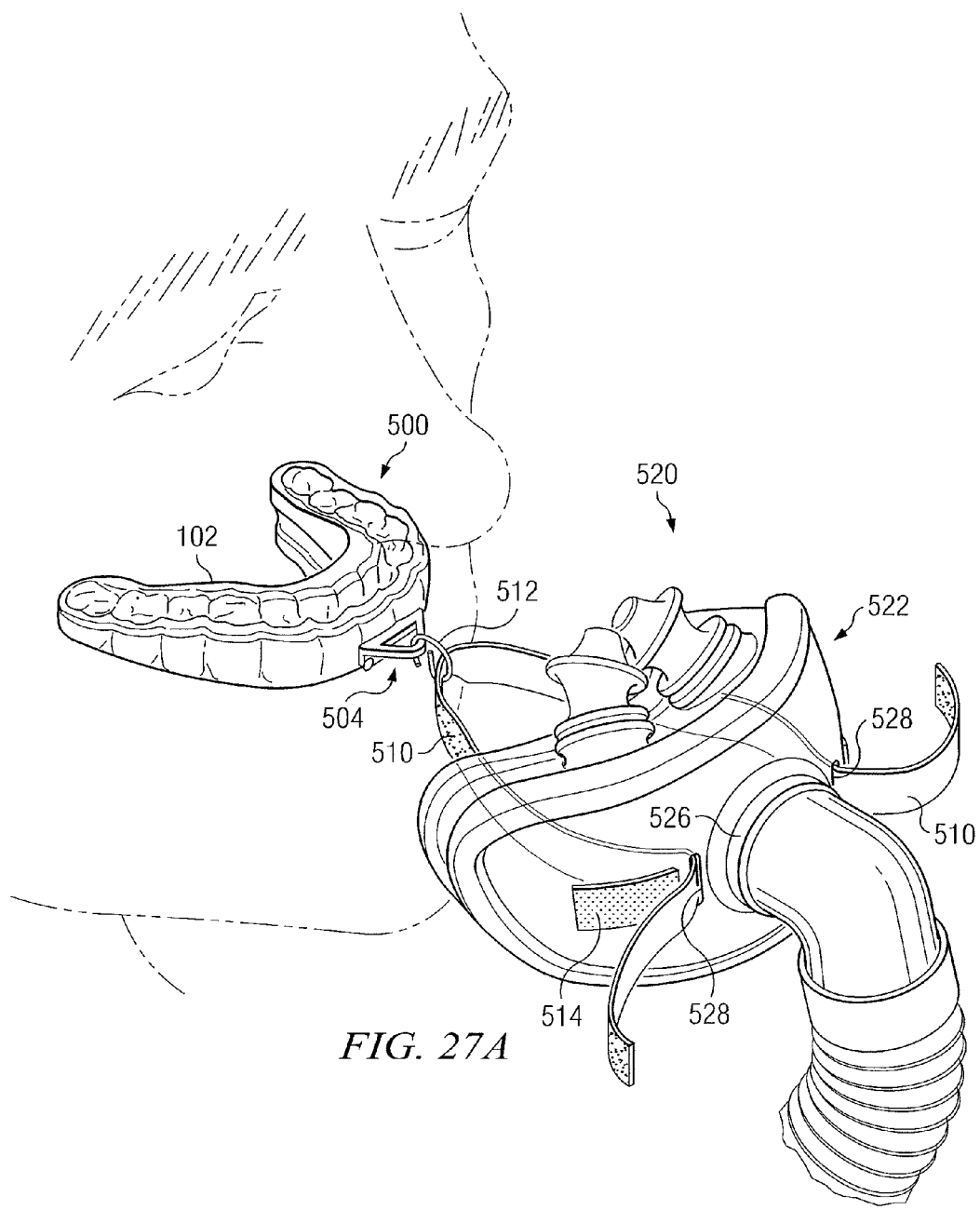
FIGS. 27A through 27D illustrate various views of an example oral appliance configured to cooperate with a tensioning element to adjustably position a gas delivery device against a user's face.
Figure 27B:
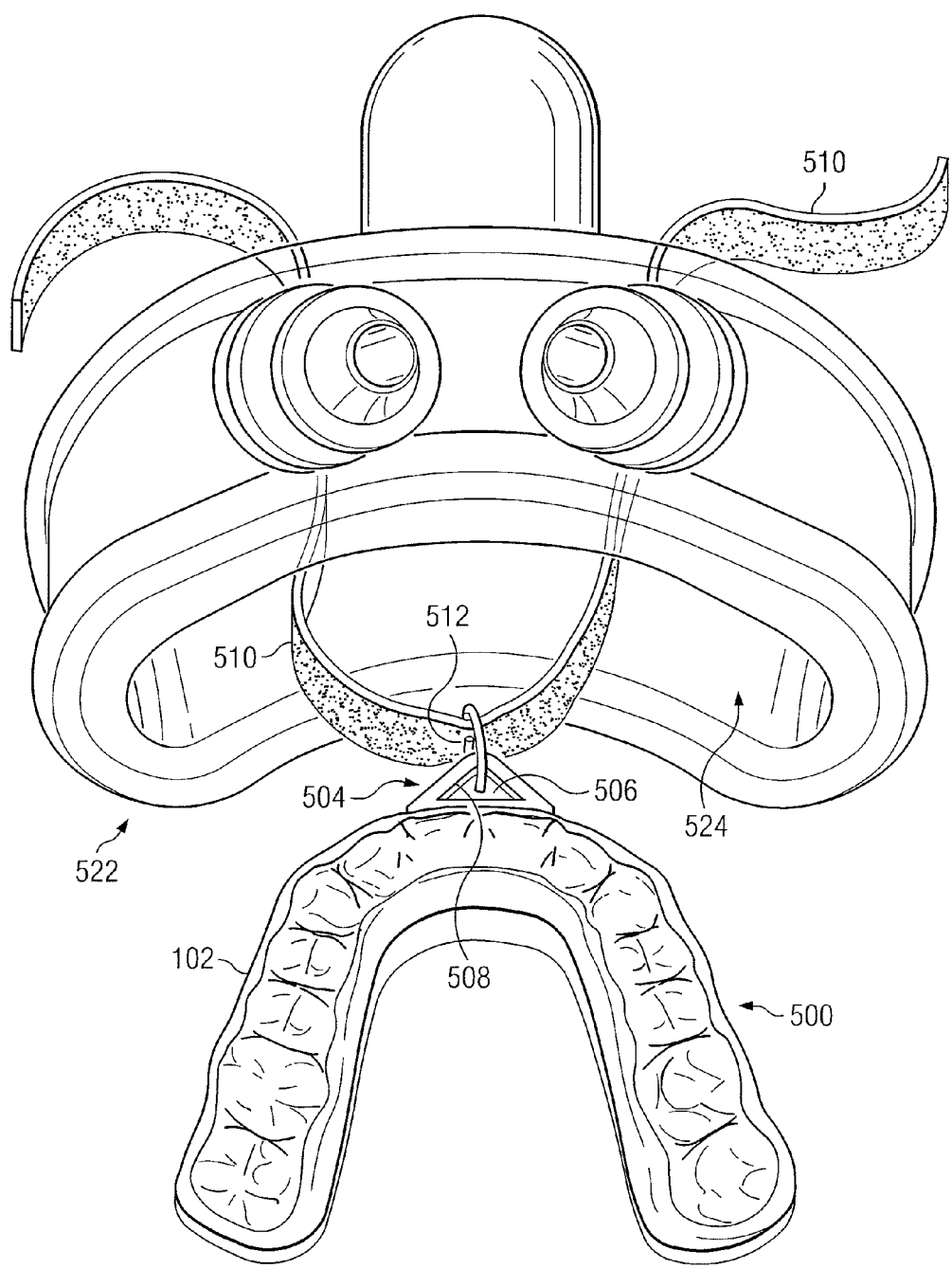
Figure 27C:
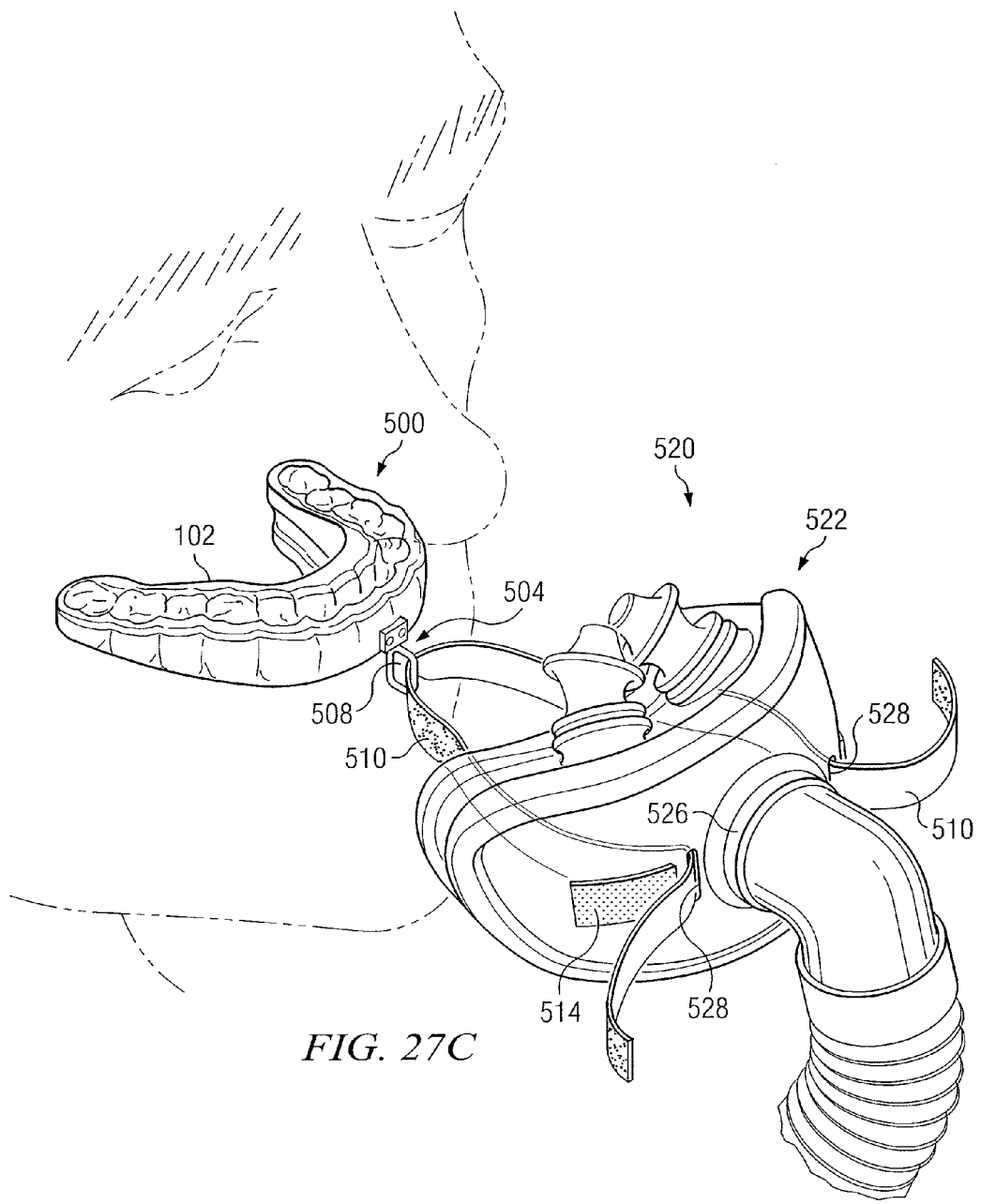
Figure 27D:
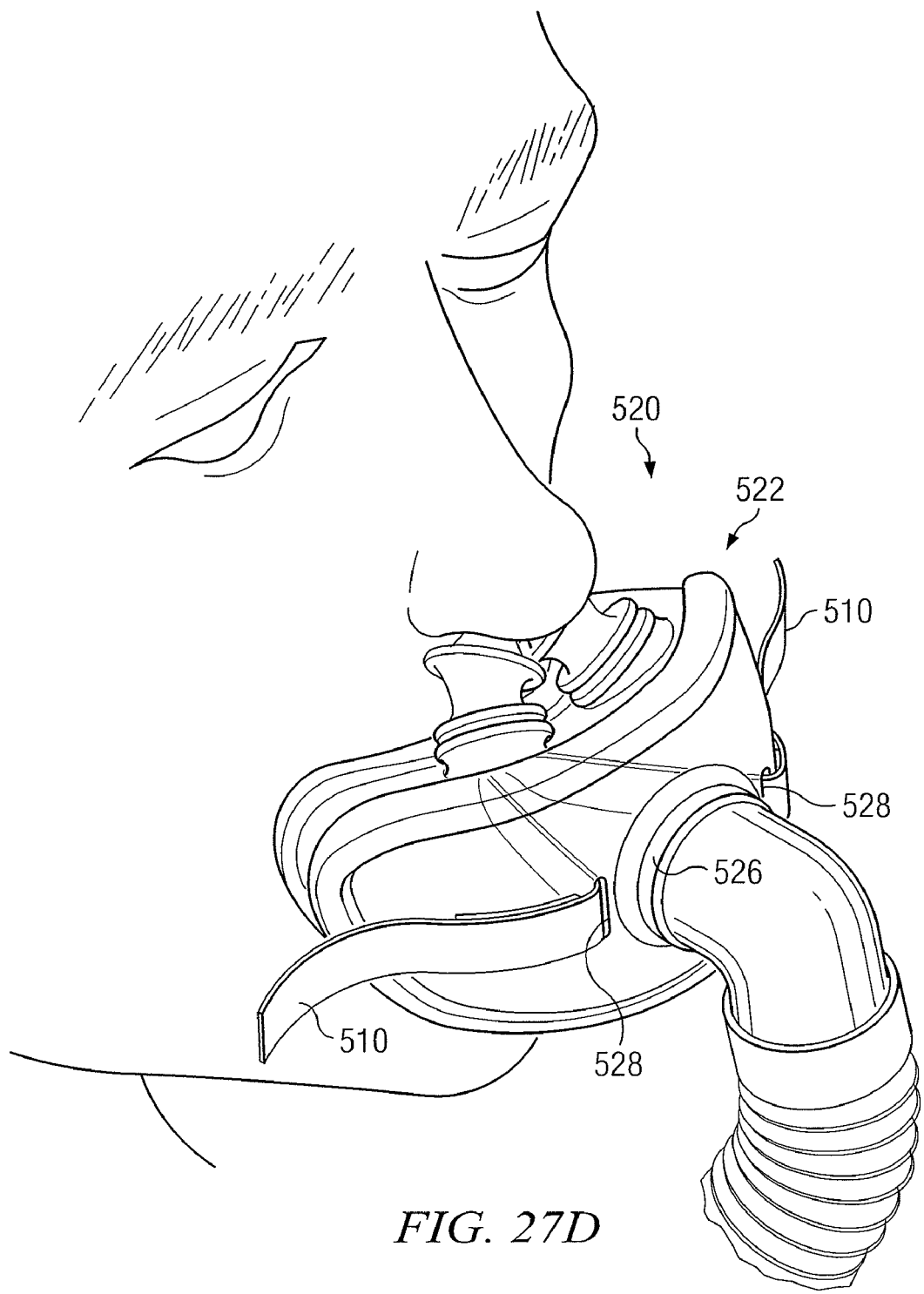

As shown in FIGS. 27A through 27C, oral appliance 500 generally includes an upper arch 102 and a forwardly extending coupler 504. Upper arch is 102 configured to receive at least some of a user's upper teeth. In certain embodiments, upper arch 102 may be substantially similar in structure and/or function to upper arch 102 of FIG. 1. In alternative embodiments, oral appliance 500 may include a lower arch 104 configured to receive at least some of the user's lower teeth, and a coupler 504 extending outwardly from the lower arch 104. In still other embodiments, oral appliance 500 may include both an upper arch 102 and a lower arch 104 coupled together, as explained further below with reference to FIG. 28.

Coupler 504 may facilitate the coupling of oral appliance 500 to flexible tension element 510. In certain embodiments, coupler 504 may have a slot 506 disposed therein. Slot 506 may be configured to receive a portion of flexible tension element 510 such as, for example, a clasp or hook 512. Flexible tension element 510 may include or engage a clasp or hook 512. As shown in FIGS. 27A and 27B, for example, slot 506 is oriented horizontally, such that a sidewall 508 of coupler 506 is configured to engage a substantially-rigid clasp or hook 512 adjustably coupled to flexible tension element 510. In certain embodiments, a coupler 504 having a horizontally-oriented slot 506, as shown in FIGS. 27A and 27B, presents a planar surface that minimizes the sensory perturbation that may arise if the user's lips contact the coupler 504. Alternative embodiments may not include a horizontally-oriented slot 506 and/or a substantially-rigid hook 512 for coupling tension element 510 to oral appliance 500. As shown in FIG. 27C, for example, coupler 504 may include a vertically-oriented slot 506 that is configured to directly receive flexible tension element 510. In particular embodiments, the vertically-oriented slot 506 may have smooth or rounded edges, thereby that minimizing the sensory perturbation that may arise if the user's lips contact the coupler 504. In an alternative embodiment, the vertically-oriented slot 506 may be tubular in shape and present an elongated surface for coupling to tension element 510.

In certain embodiments, coupler 504 may be fully integrated into, permanently coupled to, or separate and removable from upper arch 102. According to one embodiment, upper arch 102 may include one or more receptors configured to snap coupler 504 into place. In an alternative embodiment, coupler 504 may be removably coupled to upper arch 102 by one or more screws or other suitable fastener, as explained further below with reference to FIG. 29. In still another embodiment, coupler 504 may be permanently fixed to upper arch 102 by a mechanical weld, epoxy, or other suitable fastener. In yet another embodiment, upper arch 102 may be formed around at least a portion of coupler 504. According to another embodiment, upper arch 102 and coupler 504 may be integrally formed together from the same material. The components of coupler 504 may be made from any suitable material such as, for example, a biocompatible metal or hard plastic.

Flexible tension element 510 may be used to apply a tensile force that adjustably tightens and positions a mask 522 of gas delivery system 520 against the user's face. The tensile force may, for example, be directed towards the mesial plane of the user's head and towards coupler 504. In certain embodiments, flexible tension element 510 may include one or more springs, strings, cables, flexible wire, straps, other substantially pliable materials capable of flexing and applying tensile force, or any combination of the preceding. At least a portion of flexible tension element 510 may be disposed between oral appliance 500 and mask 522. In particular embodiments, at least a portion of flexible tension element 510 may be disposed within a chamber 524 at least partially or completely enclosed by a concave interior surface of mask 522.

In various embodiments, the magnitude of the tensile force applied by flexible tension element 510 may be a function of an adjusted length of flexible tension element 510 disposed between oral appliance 500 and mask 522. If flexible tension element 510 includes a spring, for example, the magnitude of the tensile force exerted by flexible tension element 510 may be a function of the distance the spring is stretched. As another example, if flexible tension element 510 includes a flexible strap, the magnitude of the tensile force applied using flexible tension element 510 may increase as the strap is cinched tighter, thereby causing a decrease in length of the portion of flexible tension element 510 disposed between oral appliance 500 and mask 522.

Mask 522 generally directs gas from gas delivery system 520 to the user. In particular embodiments, mask 522 may fit over the patient's nose, mouth and/or other portions of the patient's face or may include nasal inserts or nose pillows to direct gas directly into the patient's nasal passages. In certain embodiments, mask 522 may be optimally positioned using flexible tension element 510 to form a comfortable, substantially airtight seal. Although not intended to be exclusive, example masks 522 are described in one or more of U.S. Patent Publication Nos. 2007/0006879 and 2008/0006273, each of which is incorporated herein by reference. According to one embodiment, mask 522 may be substantially similar to at least a portion of the Mirage Liberty™ mask produced by ResMed Corporation, which may be modified to couple to flexible tension element 510.

As shown in FIGS. 27A through 27D, mask 522 may include one or more openings 528 through which a portion of flexible tension element 510 may extend. In certain embodiments, mask 522 may be adjustably positioned and tightened against the user's face by pulling on the portions of flexible tension element 510 extending through mask 522. A desired fit may be maintained by removably fastening a portion of flexible tension element 510 in place. As shown in FIGS. 27A though 27D, for example, the hook or loop side of a hook-and-loop fastener 514 may be disposed on an outer surface of mask 522 and may be configured to grip a portion of flexible tension element 510 extending outside of mask 522. Although FIGS. 27A through 27D illustrate a hook-and-loop fastener 514, any suitable fastener may be used such as, for example, a clamp, a cinch, a snap, a button, a clasp, a grommet, a threaded insert, other fastener, or any combination of the preceding. Openings 528 may be fitted with gaskets or other elements to prevent the flow of air or gas through openings 528 when in use.

Particular masks 522 may include a fitting 526 configured to receive gas provided by gas delivery system 520. For example, gas delivery system 520 may include a positive air pressure device, such as a constant positive air pressure (CPAP) system or bi-level positive air pressure (BiPAP) system. Although CPAP and BiPAP are used as examples, other systems for delivering air or other gases at constant or varying pressure may be used. Such systems may deliver any breathable gas, such as air, oxygen, anesthetics, other medical gases, other breathable gas, or any combination of the preceding. It should be understood that the term "gas" is intended to include air.

Figure 28:
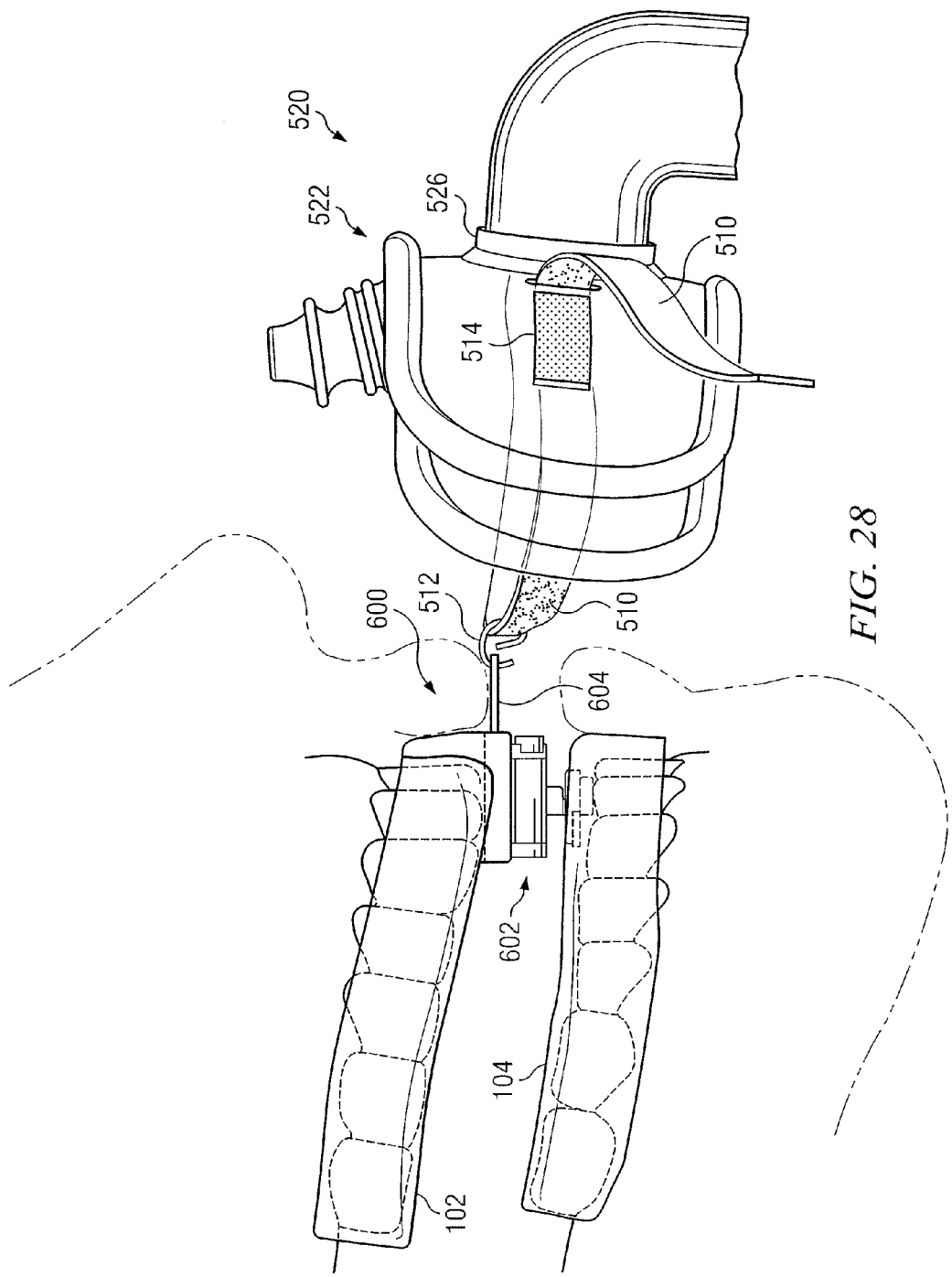
FIG. 28 illustrates a dual-arch oral appliance configured to cooperate with a flexible tensioner to adjustably position a mask 522 of a gas delivery system against a user's face.

FIG. 28 illustrates a dual-arch oral appliance 600 configured to cooperate with a flexible tension element 510 to adjustably position a mask 522 of a gas delivery system 520 against a user's face. In general, oral appliance 600 may be used to treat sleep disordered breathing, such as snoring or obstructive sleep apnea, through forward adjustment of the user's lower jaw relative to the upper jaw. This forward adjustment opens the breathing passage more fully and facilitates improved breathing through the user's nose and mouth. In certain embodiments, oral appliance 600 remains entirely within the user's mouth and surfaces of oral appliance 600 that may contact the interior of the user's mouth are smooth to prevent injury or discomfort.

In the illustrated embodiment, oral appliance 600 includes an upper arch 102 configured to receive at least some of a user's upper teeth, a lower arch 104 configured to receive at least some of the user's lower teeth, and an adjustment mechanism 502. In certain embodiments, upper arch 102 and lower arch 104 may be substantially similar in structure and function to upper arch 102 and lower arch 104 of FIG. 1.

An adjustment mechanism 602 couples lower arch 104 to upper arch 102 and may be adjusted to pull lower arch 104 forward to facilitate improved breathing. This forward adjustment may open the breathing passage more fully and may facilitate improved breathing through the user's nose and mouth. In particular embodiments, adjustment mechanism 602 may also vertically position lower arch 104 relative to upper arch 102 to determine the opening of the user's lower jaw. The components of adjustment mechanism 602 may be made from any suitable material such as, for example, a biocompatible metal or hard plastic. In the illustrated embodiment, adjustment mechanism 602 includes plate 604 substantially similar in structure and function to coupler 504 of FIGS. 27A through 27C.

Figure 29:
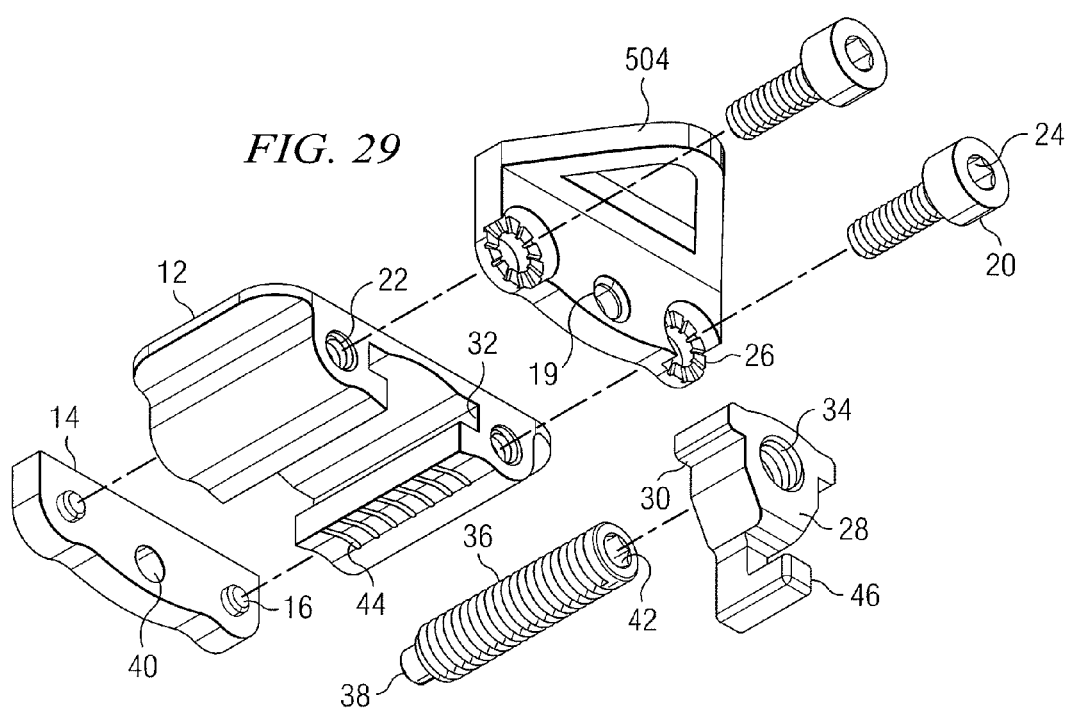
FIG. 29 illustrates an example adjustment mechanism utilizing an alternative coupler that couples to a tensioning element.

FIG. 29 illustrates an example adjustment mechanism 602 for use with oral appliance 600. In certain embodiments, adjustment mechanism 602 may include body 12, hook 28, adjustor 36, and receiver 50 (shown in FIG. 3). Body 12, hook 28, adjustor 36, and receiver 50 are discussed previously with reference to FIGS. 2A through 5B. As shown in FIG. 29, coupler 504 may removably couple to body 12 in a manner substantially similar to the front plate 18 of FIG. 3. In this manner, front plate 18 and coupler 504 may be interchanged as desired to accommodate a variety of different applications.

Particular embodiments may provide a customizable kit that includes a set of differently configured hooks 28, adjustors 36, receives 50, rear plates 14, front plates, couplers 504, adjustment mechanism 602, other elements described previously with reference to oral appliance 100 and/or oral appliance 500, or any combination of the preceding.

Particular embodiments may provide gas to a user in a manner that improves the user's breathing and that also enhances comfort for the user. For example, particular flexible tension elements 510 may adjustably tighten and optimally position a gas delivery system 520 against a user's face without the use of elements that wrap around the user's head and that may come in contact with the user's skin and hair. In addition, certain flexible tension elements 510 may be configured to adjustably reposition a gas delivery system 520 along multiple axes. For example, the mask may be optimally repositioned relative to the user's face along a left-right axis, an up-down axis, and/or an axis disposed between left-right and up-down axis. In certain embodiments, flexible tension element 510 may absorb various forces caused by the movement of gas delivery system 520, such that the transfer of such forces to oral appliance 500 may be minimized. For example, if horizontal or vertical force is applied to mask 522, it will not transfer a moment force to the user, as may occur with a coupler that is not flexible. Particular flexible tension elements 510 may be configured to automatically redistribute forces, such that forces are evenly distributed along surfaces where gas delivery system 520 comes in contact with a user's face. For example, by applying a tensile force towards the center of mask 522, the force applied along the periphery of mask 522 in contact with user's face may be evenly distributed to custom fit to user's facial features.

Although the present invention has been described in connection with several embodiments, it should be understood that a myriad of changes, substitutions, variations, alterations, transformations, and modifications may be suggested to one of skill in the art, and it is intended that the present invention encompass such changes, substitutions, variations, alterations, transformations, and modifications as fall within the spirit and scope of the appended claims.

What is claimed is:

1. A kit for use in constructing an oral appliance for treating a breathing condition, the kit comprising:
   an adjustment mechanism configured to adjustably couple a first dental arch to a second dental arch and displace the second dental arch in a forward position relative to the first dental arch; and
   a plurality of plates each configured to removeably couple to a body of the adjustment mechanism;
   wherein the plurality of plates comprise at least two plates that are not structurally identical with respect to each other;
   wherein at least one of the plurality of plates is configured to couple a tensioning device to the oral appliance, the tensioning device configured to adjustably couple a mask to the oral appliance, the tensioning device comprising a flexible tension element configured to apply an adjustable tensile force between the mask and the oral appliance.

2. The kit of claim 1, wherein the adjustment mechanism comprises:
   a front stop, a rear stop, and a guide extending between the front stop and rear stop;
   a threaded member configured to be coupled between the front stop and rear stop of the body and configured to rotate relative to the body; and
   a hook configured to be coupled to the guide, comprising a threaded passage configured to engage the threaded member, and comprising an arm configured to engage the second dental arch, the hook configured to travel in a forward direction along the guide between the front stop and rear stop of the body in response to rotational adjustment of the threaded member to adjust the second dental arch to an optimum position in the forward direction for a particular user's anatomy and breathing condition.

3. The kit of claim 1, wherein the one of the plurality of plates comprises a horizontally-oriented slot.

4. The kit of claim 1, wherein the one of the plurality of plates comprises a vertically-oriented slot.

5. The kit of claim 1, wherein the one of the plurality of plates comprises a post.

6. The kit of claim 1, wherein:
   the one of the plurality of plates comprises a horizontally-oriented slot;
   a second one of the plurality of plates comprises a vertically-oriented slot; and
   a third one of the plurality of plates comprises a post.

7. The kit of claim 1, wherein the kit further comprises a plurality of hooks each configured to removeably couple to the body of the adjustment mechanism, a first hook of the plurality of hooks comprising an arm having a length substantially different from a corresponding length of an arm of a second hook of the plurality of hooks.

8. The kit of claim 1, wherein the kit further comprises a plurality of receivers each configured to removeably couple engage a hook coupled to the body of the adjustment mechanism.

* * * * *